(12) United States Patent
Kore et al.

(10) Patent No.: US 8,344,118 B2
(45) Date of Patent: *Jan. 1, 2013

(54) PREPARATION AND ISOLATION OF 5' CAPPED MRNA

(75) Inventors: Anilkumar Kore, Austin, TX (US); Shanmugasundaram Muthian, Austin, TX (US); Irudaya Charles, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/324,724

(22) Filed: Dec. 13, 2011

(65) Prior Publication Data

US 2012/0156751 A1 Jun. 21, 2012

Related U.S. Application Data

(63) Continuation of application No. 12/771,495, filed on Apr. 30, 2010, now Pat. No. 8,093,367, which is a continuation of application No. PCT/US2008/081651, filed on Oct. 29, 2008.

(60) Provisional application No. 60/984,320, filed on Oct. 31, 2007.

(51) Int. Cl.
*C07H 21/00* (2006.01)
*B01L 3/00* (2006.01)
*C12Q 1/68* (2006.01)
*G01N 15/06* (2006.01)

(52) U.S. Cl. ............ 536/23.1; 536/25.3; 536/26.6; 435/6.1; 435/325; 422/68.1; 422/430

(58) Field of Classification Search ............ 536/23.1, 536/25.3, 26.6; 435/6.1, 325; 422/68.1, 422/430

See application file for complete search history.

(56) References Cited

U.S. PATENT DOCUMENTS 8,093,367 B2 * 1/2012 Kore et al. ............ 536/23.1

* cited by examiner

*Primary Examiner* — Jezia Riley

(57) ABSTRACT

The synthesis of capped/tagged RNA, methods of use and kits providing same are contemplated. Tagged RNA permits isolation of RNA transcripts in vitro. The ability to isolate and purify capped RNA results in improved transcription and translation and provides a tool for identifying RNA-protein interactions. Such capped RNA finds use in therapeutic applications, diagnosis and prognosis and in the treatment of cancers and HIV.

20 Claims, 11 Drawing Sheets

$R_2$ = OH, OCH$_3$, deoxy
n = 2 m$^7$G[5']pppp[5']U-S-S-BIOTIN

R₂ = OH, OCH₃, deoxy
n = 2 m⁷G[5']pppp[5']U-S-S-BIOTIN

Bio-18UTP:

Bio-16UTP:

Bio-11UTP:

L = Nucleotide Size Ladder;   1 = Control RNA, No Cap;

2 = m$^7$GpppG;   3 = m$^7$GppppG;   4 = GppppU-AA;

5 = m$^7$GppppU-AA;   6 = m$^7$GppppU-18-Biotin

PREPARATION AND ISOLATION OF 5' CAPPED MRNA

CROSS-REFERENCE TO RELATED APPLICATIONS

This application is a continuation of U.S. application Ser. No. 12/771,495 filed on Apr. 30, 2010 now U.S. Pat. No. 8,093,367, which is a continuation of International Application No. PCT/US08/081651, filed on Oct. 29, 2008, which application claims the benefit of U.S. Provisional Application No. 60/984,320, filed on Oct. 31, 2007. Said applications are incorporated herein by reference in their entirety.

The section headings used herein are for organizational purposes only and should not be construed as limiting the subject matter described herein in any way.

INTRODUCTION

Eukaryotic mRNAs bear a "cap" structure at their 5'-termini that is well known to play an important role in translation. Naturally occurring cap structures comprise a 7-methyl guanosine that is linked via a triphosphate bridge to the 5'-end of the first transcribed nucleotide, resulting in $m^7G(5')ppp(5')$N, where N is any nucleoside (Nuc). The mRNA cap plays an important role in gene expression. It protects the mRNAs from degradation by exonucleases, enables transport of RNAs from the nucleus to the cytoplasm and participates in assembly of the translation initiation complex. $m^7G(5')ppp(5')G$ (mCAP) has been used as the dinucleotide cap in transcription with T7 or SP6 RNA polymerase in vitro to obtain RNAs having a cap structure in their 5'-termini. In vivo, the cap is added enzymatically. However, over the past 20 years or so, numerous studies have required the synthesis of proteins in an in vitro translation extract supplemented with in vitro synthesized mRNA. The prevailing method for the in vitro synthesis of capped mRNA employs a pre-formed dinucleotide of the form $m^7G(5')ppp(5')G$ ($m^7GpppG$) as an initiator of transcription. A disadvantage of using mCAP, a pseudosymmetrical dinucleotide, has always been the propensity of the 3'-OH of either the G or $m^7G$ ($m^7Guo$) moiety to serve as the initiating nucleophile for transcriptional elongation. This leads to the synthesis of two isomeric RNAs of the form $m^7G(5')pppG(pN)_n$ and $G(5')pppm^7G(pN)_n$, in approximately equal proportions, depending upon the ionic conditions of the transcription reaction. This may be problematic for various downstream processes, such as in vitro translation or crystallization studies.

To date, the usual form of a synthetic dinucleotide cap used in in vitro translation experiments is the ARCA. The Anti-Reverse Cap Analog (ARCA) is most often a modified cap analog in which the 3' OH group is replaced with $OCH_3$. ARCA and triple-methylated cap analogs are incorporated in the forward orientation. The selective procedure for methylation of guanosine at N7 and 3' O-methylation and 5' diphosphate synthesis has been established (Kore, A. and Parmar, G. *Nucleosides, Nucleotides, and Nucleic Acids,* 25:337-340, (2006) and Kore, A. R., et al. *Nucleosides, Nucleotides, and Nucleic Acids* 25(3): 307-14, (2006).

In the cell, the cap is added in the nucleus and is catalyzed by the enzyme guanylyl transferase. The addition of the cap to the 5' terminal end of RNA occurs after initiation of transcription but immediately after transcription initiation so that it is almost impossible to detect. The terminal nucleoside is always a guanosine, and is in the reverse orientation to all the other nucleotides, i.e., $G(5')ppp(5')GpNpNp$ ... and the cap contains two nucleotides, connected by a 5'-5' triphosphate linkage.

Transcription of RNA usually starts with a nucleoside triphosphate (usually a purine, A or G). When transcription occurs in vitro, it typically comprises a phage RNA polymerase such as T7, T3 or SP6, a DNA template containing a phage polymerase promoter, nucleotides (ATP, GTP, CTP and UTP) and a buffer containing magnesium salt. The synthesis of capped RNA includes the incorporation of a cap analog (e.g., N7 methyl GpppG or $m^7GpppG$) in the transcription reaction. Excess $m^7GpppG$ to GTP (4:1) favors to increase the opportunity that each transcript will have a 5' cap. The mMESSAGE mMACHINE® kit from Ambion (Ambion, Inc., Austin, Tex., a business of Applied Biosystems) recommends this ratio and will typically yield 80% capped RNA to 20% uncapped RNA, although total RNA yields are lower as GTP concentration becomes rate limiting as GTP is needed for the elongation of the transcript. However, the transcription reaction products contain unincorporated NTPs, enzymes and buffer components as well as uncapped RNA transcripts which interfere with translation efficiency and protein yield.

The recent literature reveals that chemical modification of m7Guo at either the 2' or 3' OH group of the ribose ring results in the cap being incorporated solely in the forward orientation, even though the 2' OH group does not participate in the phosphodiester bond. However, currently there is no technology/method available, which will allow researchers and developers of RNA therapeutics to selectively isolate only capped RNA from uncapped fragments. In order to overcome this barrier, disclosed herewith are novel cap analogs which have been designed and synthesized with reporter moieties allowing purification and isolation of only the capped RNA transcript. Clearly, the art is in need of a novel method of synthesizing dinucleotide cap analogs with a reporter moiety and isolation protocols. The creative use of affinity tags as the reporter moiety will provide a simple and skillful means to isolate and purify capped RNA transcripts from the transcription reaction mixture.

The discovery of a method of synthesizing dinucleotide cap analogs with a reporter moiety attached, the attachment of a reporter moiety to a dinucleotide cap post-transcription, and the subsequent retrieval and purification of the capped RNA transcript is disclosed herein. Experiments in which the reporter moiety-labeled RNA transcript was isolated from the transcription reaction followed by cleavage of the reporter moiety from the tagged RNA to yield purified capped RNA transcripts show that the capped RNA transcripts are successfully transfected and have demonstrated improved translation efficiency and protein yields when compared to RNA caps without a reporter moiety attached.

The structure of the novel cap analogs were confirmed by $^1H$ NMR, $^{31}P$ NMR, and mass spectroscopy. Methods to isolate and purify capped RNA transcripts were developed using biotin as the affinity tag. Standard in vitro transcription reactions were performed by using pTri β actin vector in the presence of T7 RNA polymerase and the novel cap analogs. Capping assays indicate that these new caps are substrates for T7 RNA polymerase.

Because the 5' cap structure enhances the translation of mRNA by helping to bind the eukaryotic ribosome and assuring recognition of the proper AUG initiator codon, providing purified capped RNA assists in translation efficiency. Capped RNA encoding specific genes can be transfected into eukaryotic cells or microinjected into cells or embryos to study the effect of the translated product in the cell or embryo. If uncapped RNA is used, the RNA in these experiments is rapidly degraded and the yield of translated protein is substantially reduced. The capped RNA transcript finds use in both in vivo and in vitro translation studies. These results provide important improvements in therapeutic delivery mechanism, vaccine production, diagnoses and RNA-protein interaction studies as well as providing efficient use of often limited RNA samples, thereby conserving and extending sample availability.

The synthesis of capped RNA efficiently to yield high levels of transcribed RNA is an area of unmet need as is the need to isolate and purify capped RNA molecules in vitro, ideally, capped RNAs with caps in the proper orientation. Thus, there exists in the art a need for high yield transcription reactions that efficiently synthesize RNA. The resulting RNA finds use in a variety of applications, including ribozyme, antisense and biophysical studies, and gene array analysis. Additionally, capped RNA transcripts are used for applications requiring protein synthesis such as in vivo expression (e.g., microinjection, transfection and infection experiments) and in vitro translation. Thus, the instant application provides novel technological improvements having important applications in universal labeling and detection, therapeutics, diagnostics, and vaccine development.

SUMMARY

In one aspect, provided herein is a dinucleotide cap analog useful for specifically transcribing an mRNA molecule of interest. The dinucleotide cap analog composition comprises:

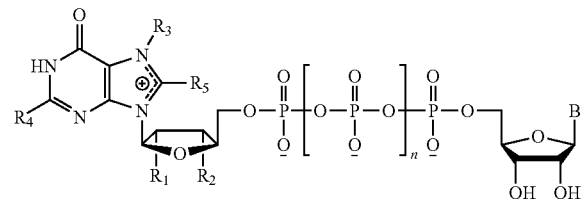

wherein: B is a nucleobase; $R_1$ is selected from a halogen, OH, and $OCH_3$; $R_2$ is selected from H, OH, and $OCH_3$; $R_3$ is $CH_3$ or void; $R_4$ is $NH_2$; $R_5$ is H; and n is 1, 2 or 3; wherein a linker is attached to one of $R_1$, $R_2$, $R_4$, $R_5$, or B and $R_1$ or $R_2$ is OH.

The nucleobase can be a nucleobase or nucleobase analog that is operative in accordance with the various compositions and methods described herein. In some embodiments, the nucleobase can be a purine, purine analog, pyrimidine, pyrimidine analog and natural, synthetic and derivatives thereof. In some embodiments, the nucleobase can be adenine, adenine analogs and natural, synthetic and derivatives thereof. In some embodiments the nucleobase can be uracil, uracil analogs and natural, synthetic and derivatives thereof. In yet other embodiments, the nucleobase can be guanine, guanine analogs and natural, synthetic and derivatives thereof.

In some embodiments, the linker can be N, S, and O. In some embodiments, the linker can be an aminoallyl ($[-CH_2]_n$ $CH_2NH_2$) where n=2-18, a secondary amine and an alkyl ($C_3$-$C_{10}$)$NH_2$ chain. In some embodiments the alkyl chain can comprise three to ten chain atoms with a terminal primary amine. In some embodiments the linker can be a cleavable or can be a non-cleavable linker. In such embodiments, the linker can be attached by a first end to the nucleobase and can have a second end with a reactive group which can be available for binding to a reporter moiety. In some embodiments, the linker can be covalently linked to the nucleobase. In some embodiments, if the nucleobase comprises a purine base, the linker can be attached to the 2-position ($R_4$) or 8-position ($R_5$) of the purine, if the nucleobase comprises a 7-deazapurine base, the linker moiety can be attached to the 7-position of the 7-deazapurine, and if the nucleobase comprises a pyrimidine base, the linker moiety can be attached to the 5-position of the pyrimidine. In some embodiments the linker moiety can be attached to the 2' or 3' position of the ribose ring attached to the methylated 7-position of the guanine.

The reporter moiety can be attached to the linker at the linker's reactive group. The reporter moiety can be any moiety capable of binding to a substrate, for example, a magnetic bead, a chromatography column bound with, for example, avidin, streptavidin, antigen, antibody, and the like. In some embodiments, the reporter moiety can be an affinity tag or an epitope tag. In further embodiments, the affinity tag can be selected from biotin, iminobiotin, avidin, and streptavidin. Non-limiting examples of biotin molecules that can comprise the reporter moiety include $C_5$-$C_{20}$-biotin, SS-biotin, XX-biotin, and NHS ester compounds thereof.

In another aspect, the dinucleotide cap analog is useful in the transcription of DNA to mRNA and the subsequent purification of the transcribed mRNA. In some embodiments the dinucleotide cap analog is attached to the 5' end of an RNA molecule. In such embodiments, the cap analog can facilitate the isolation and purification of capped, transcribed RNA from a transcription reaction mixture.

Also provided is a method of synthesizing a detectable dinucleotide cap analog comprising: a) providing a guanosine nucleoside optionally comprising either a 2' substituent or a 3' substituent and optionally comprising a linker; b) phosphorylating the first nucleoside, forming a first nucleotide; c) methylating the first nucleotide; d) adding a phosphorylated second nucleotide optionally comprising a linker; e) coupling said first nucleotide with said second nucleotide, forming a dinucleotide cap analog. In one embodiment a reporter moiety can be attached to said linker. In some embodiments the first nucleotide can be guanosine, which can be methylated at the N7 position. In various embodiments the 2' substituent of said first nucleotide can be a halogen, OH or $OCH_3$ and the 3' substituent of said first nucleotide can be OH or $OCH_3$. In some embodiments one of the 2' or 3' substituents is OH. In some embodiments the halogen can be fluorine. In some embodiments the coupling of the first and second nucleotides can be catalyzed by $ZnCl_2$.

Also provided is a method for isolating a dinucleotide capped molecule comprising: a) providing a nucleic acid mixture containing a dinucleotide cap analog attached to the 5' end of an RNA molecule. In some embodiments, the 5' capped RNA molecule is present in a purified form. In some embodiments, the capped RNA can be isolated by use of a reporter moiety attached to a linker attached to the RNA cap analog; b) binding the reporter moiety of step a) to a substrate; c) extracting the complex of step b) from the nucleic acid mixture; and optionally, d) removing the reporter moiety from the capped nucleic acid; wherein capped nucleic acids are isolated.

Also provided is a composition comprising: an antigen presenting cell transfected with a capped nucleic acid obtained by a) providing a nucleic acid mixture containing a dinucleotide cap analog attached to the 5' end of an RNA molecule. In some embodiments, the 5' capped RNA molecule is present in a purified form. In some embodiments, the capped RNA can be isolated by use of a reporter moiety attached to a linker attached to the RNA cap analog; b) binding the reporter moiety of step a) to a substrate; c) extracting the complex of step b) from the nucleic acid mixture; and d) removing the linker from the capped nucleic acid; wherein capped nucleic acids are isolated.

Also provide is a composition comprising an antigen presenting cell transfected with a dinucleotide cap analog attached to the 5' end of an RNA molecule. In some embodiments, the 5' capped RNA molecule is present in a purified form. In some embodiments, the capped RNA can be isolated by use of a reporter moiety attached to a linker attached to the RNA cap analog. The reporter moiety can be any moiety capable of binding to a substrate, for example, a magnetic bead, a chromatography column bound with, for example, avidin, streptavidin, antigen, antibody, and the like. Such a reporter moiety can be an affinity tag or an epitope tag. In some embodiments, the affinity tag can be selected from biotin, iminobiotin, avidin, and streptavidin. Non-limiting examples of biotin molecules that can comprise the reporter moiety include $C_5$-$C_{20}$-biotin, SS-biotin, XX-biotin, and NHS ester compounds thereof.

Also provide is a dinucleotide cap analog within a cell. In some embodiments the first nucleotide of the cap can be guanosine, which can be methylated at the N7 position. In some embodiments the nucleobase of the second nucleotide can be a purine or a pyrimidine as well as natural, synthetic and derivative nucleobases thereof. In various embodiments the 2' substituent of said first nucleotide can be a halogen, OH or $OCH_3$ and the 3' substituent of said first nucleotide can be H, OH or $OCH_3$. In some embodiments one of the 2' or 3' substituents is OH. In some embodiments the halogen can be fluorine. In some embodiments the dinucleotide cap analog is attached to the 5' end of an RNA molecule. In some embodiments, the 5' capped RNA molecule is present in a purified form. In some embodiments, the capped RNA can be isolated by use of a reporter moiety attached to a linker attached to the RNA cap analog. The reporter moiety can be any moiety capable of binding to a substrate, for example, a magnetic bead, a chromatography column bound with, for example, avidin, streptavidin, antigen, antibody, and the like. Such reporter moiety can be an affinity tag or an epitope tag. In some embodiments, the affinity tag can be selected from biotin, iminobiotin, avidin, and streptavidin. Non-limiting examples of biotin molecules that can comprise the reporter moiety include $C_5$-$C_{20}$-biotin, SS-biotin, XX-biotin, and NHS ester compounds thereof.

Generally, the present teachings include dinucleotide CAP analog compounds having attached thereto a reporter moiety. Such detectable dinucleotide CAP analogs when attached to an RNA molecule are useful in identification, quantification, and purification/isolation of capped RNA, purification of transcribed RNA, in the expression of proteins, transfection of dendritic cells, synthesis of vaccines and protein production within, for example, HeLa cells, identification of RNA-protein interactions, for the identification of RNA, in the analysis of proteins, and in methods utilizing such CAP analogs and reagents in the area of therapeutics, diagnostics and prognostics. The disclosed compounds of the present teachings may find particular application in the area of purification of capped RNA, RNA transfection into dendritic cells, vaccine development, therapeutics and diagnostics Also provided are kits for performing methods of the present teachings. For example, in some embodiments the kits include a dinucleotide cap analog useful for specifically transcribing an mRNA molecule of interest. The dinucleotide cap analog composition comprises:

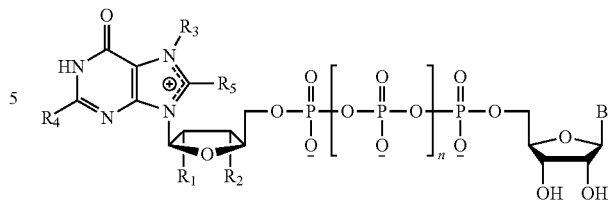

wherein: B is a nucleobase; $R_1$ is selected from a halogen, OH, and $OCH_3$; $R_2$ is selected from H, OH, and $OCH_3$; $R_3$ is $CH_3$ or void; $R_4$ is $NH_2$; $R_5$ is H; and n is 1, 2 or 3; wherein a linker is attached to one of $R_1$, $R_2$, $R_4$, $R_5$, or B and an RNA polymerase.

In various embodiments, the kits can include a reporter moiety, attached to the linker found within the dinucleotide cap analog composition, useful for isolation and purification of transcribed mRNA. In some embodiments, the kits include nucleotides, ribonuclease inhibitor and DNase. In some embodiments, the kits include an enzyme such as an RNA polymerase, including but not limited to SP3, SP6 and T7 polymerases, and a buffer, such as enzyme or nucleotide buffers. In some embodiments the reporter moiety within the kits is selected from an affinity tag and an epitope tag. In some embodiments, the reporter moiety can be an affinity tag such as biotin.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DESCRIPTION OF VARIOUS EMBODIMENTS

Figure 1:
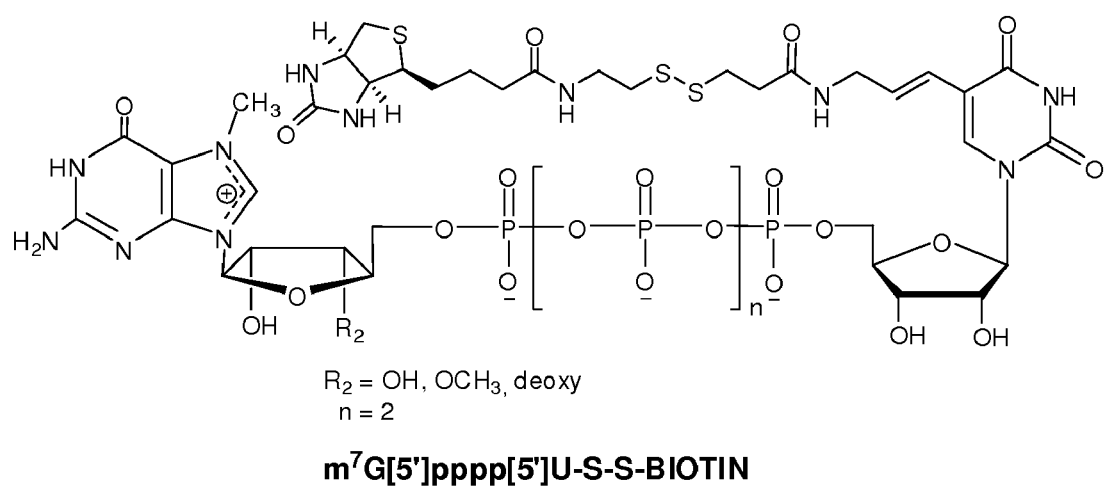
FIG. 1 provides the general structure of a biotin-labeled mCAP analog.

It is to be understood that both the foregoing general description and the following description are exemplary and explanatory only and are not restrictive of the compositions and methods described herein.

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting.

As used herein, the term "affinity tag" refers to a moiety that can be attached to a nucleotide or nucleotide analog, and that is specifically bound by a partner moiety. The interaction of the affinity tag and its partner provides for the detection of molecules bearing the affinity tag. Examples include, but are not limited to biotin or iminobiotin and avidin or streptavidin. A sub-class of affinity tag is the "epitope tag," which refers to a tag that is recognized and specifically bound by an antibody or an antigen-binding fragment thereof.

As used herein, the term "alkyl" refers to a saturated or unsaturated, straight-chain, branched, or cyclic hydrocarbon radical derived by the removal of one hydrogen atom from a single carbon atom of a parent alkane, alkene, or alkyne. Typical alkyl groups include, but are not limited to, methyl, ethyl, propyl, butyl, and the like. Typical alkyl groups include, but are not limited to, methyl (—CH$_3$); ethyls such as ethanyl (—CH$_2$—CH$_3$), ethenyl (—CH=CH$_2$), ethynyl (—C≡CH); propyls such as propan-1-yl (—CH$_2$—CH$_2$—CH$_3$), propan-2-yl, cyclopropan-1-yl, prop-1-en-1-yl (—CH=CH—CH$_3$), prop-1-en-2-yl, prop-2-en-1-yl (—CH$_2$—CH=CH$_2$), prop-2-en-2-yl, cycloprop-1-en-1-yl; cycloprop-2-en-1-yl, prop-1-yn-1-yl (—C≡C—CH$_3$), prop-2-yn-1-yl (—CH$_2$—C≡CH), etc.; butyls such as butan-1-yl (—CH$_2$—CH$_2$—CH$_2$—CH$_3$), butan-2-yl, cyclobutan-1-yl, but-1-en-1-yl (—CH=CH—CH$_2$—CH$_3$), but-1-en-2-yl, but-2-en-1-yl (—CH$_2$—CH=CH—CH$_3$), but-2-en-2-yl, buta-1,3-dien-1-yl (—CH=CH—CH=CH$_2$), buta-1,3-dien-2-yl, cyclobut-1-en-1-yl, cyclobut-1-en-3-yl, cyclobuta-1,3-dien-1-yl, but-1-yn-1-yl (—C≡C—CH$_2$—CH$_3$), but-1-yn-3-yl, but-3-yn-1-yl (—CH$_2$—CH$_2$—C≡CH), etc.; and the like.

As used herein, the term "aminoallyl" refers to a carbon atom chain of the formula ([—CH$_2$]$_n$CH$_2$NH$_2$) where n=2-18. The aminoallyl group is most often found attached to the 5-position of the pyrimidine ring of uracil and cytosine. When attached to a nucleotide, it can be abbreviated as "aa-UTP" or "aa-CTP".

As used herein, the term "antigen presenting cell" (APC) refers to a cell displaying an antigen-MHC complex on its surface. The T-cell receptor of T-cells may recognize the antigen. Examples of APCs include without limitation dendritic cells, macrophages, B-cells, fibroblasts (skin), thymic epithelial cells, thyroid epithelial cells, glial cells (brain), pancreatic beta cells, and vascular endothelial cells. (Steinman, R. M. and J. Banchereau, *Nature* 449, 419-426 (2007)) incorporated herein by reference).

As used herein, the term "cell" refers to any eukaryotic or prokaryotic cell cultured in vitro for therapeutic, diagnostic or research purposes. Cells can originate from embryos, tissues and diseased tissues, including but not limited to blood, liver, muscle, melanoma, glioblastoma, lymphoma, carcinoma, epithelium, neuroblastoma, glioblastoma, colorectal carcinoma/lung metastasis, ovarian, prostate, uterine, mammary, breast, hybridoma, kidney, prostrate, lung, heart, brain and skin. Cells can be derived and/or isolated from embryonic stem cells, B-cells, T-cells, bone marrow and so on.

As used herein, the term "ARCA" or Anti-Reverse Cap Analog refers to a modified cap analog in which the 2' and/or 3' OH group on the guanosine is replaced with—another chemical moiety. An example of an ARCA structure representation is m$_2$$^{7,3'O}$G(5')PPP(5')G. Table 1 identifies ARCAs contemplated in the current application.

As used herein, the term "cap" refers to a non-extendible dinucleotide that facilitates translation or localization, and/or prevents degradation of an RNA transcript when incorporated at the 5' end of an RNA transcript, typically having an m$^7$GpppG or m$^7$GpppA structure. In nature the modified base 7-methylguanosine is joined in the opposite orientation, 5' to 5' rather than 5' to 3', to the rest of the molecule via three phosphate groups i.e., P1-guanosine-5'-yl P3-7-methylguanosine-5'-yl triphosphate (m$^7$G5'ppp5'G). The cap may include a triphosphate, a tetraphosphate or a pentaphosphate group joining the two nucleotides.

As used herein, the term "cap analog" refers to a structural derivative of an RNA cap that may differ by as little as a single element.

As used herein, the term "mCAP" refers to a dinucleotide cap with the N7 position of the guanosine having a methyl group. The structure can be represented as m$^7$G(5')ppp(5')G, though a triphosphate, a tetraphosphate or a pentaphosphate group can join the two nucleotides. mCAP can used as the dinucleotide cap in transcription with T7, SP3 or SP6 RNA polymerase in vitro to obtain RNAs having a cap structure in their 5'-termini.

As used herein, the term "enzymatically incorporatable" means that a nucleotide is capable of being enzymatically incorporated onto the terminus, e.g. 3' terminus, of a polynucleotide chain, or internally through nick-translation of a polynucleotide chain, through action of a template-dependent or template-independent polymerase enzyme. A nucleotide-5'-triphosphate is an example of an enzymatically incorporatable nucleotide.

As used herein, the term "enzymatically extendable" or "3' extendable" means a nucleotide or polynucleotide that is capable of being appended to a nucleotide or polynucleotide by enzyme action. A polynucleotide containing a 3' hydroxyl group is an example of an enzymatically extendable polynucleotide.

As used herein, the term "halogen" refers to nonmetal elements of Group 7A of the Periodic Table of the Elements comprising fluorine (F), chlorine (Cl), bromine (Br), iodine (I), and astatine (At). Halogens are monovalent, readily form negative ions and occur as compounds or ions.

As used herein, the term "linker" refers to the chemical group(s) which joins a reporter moiety, e.g., an affinity tag, to a dinucleotide cap analog. The nucleobase, a ribose or analogs thereof within the dinucleotide cap analog may be modified to contain a reactive group (e.g., an amine on an aminoallyl or alkynyl amine), with a reporter moiety attached. The "linker" according to the invention is considered to be the chemical entity or entities between the dinucleotide cap and the reporter moiety. That is, the "linker" encompasses any modifying group added to the dinucleotide cap in order to provide conjugation between the dinucleotide containing linker w/primary amine and the reporter moiety having an NHS ester group for the attachment of a reporter moiety. In various embodiments, useful linkers include, but are not limited to N, S, and O, an aminoallyl ([—CH$_2$]$_n$CH$_2$NH$_2$) where n=2-18, a secondary amine and an alkyl (C$_3$-C$_{10}$)NH$_2$ chain. Linkers can include, for example, an alkyl, allyl, or alkynyl amine modifying group attached to the nucleobase. As an alternative, linkers can include one or more ethylene oxy moieties.

As used herein, the term "nucleobase" refers to a nitrogen containing heterocyclic moiety nucleobase of a nucleotide or a nucleotide analog. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine), including naturally-occurring and synthetic derivatives. Additional nucleobases that can be used in the practice of the disclosed embodiments include pyrazolo[3,4-d]pyrimidines, 5-methylcytosine, 5-hydroxymethyl cytosine, xanthine, hypoxanthine, 2-aminoadenine, 6-methyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine, 3-deazaadenine, pyrazolo[3,4-d]pyrimidine, imidazo[1,5-a]1,3,5 triazinones, 9' deaapurines, imidazo[4,5]d]pyrazines, thiazolo[4,5-d]primidines, pyrazin-2-ones, 1,2,4]triazine, pyridazine; and 1,3,5 triazine and so on. Nucleobases useful in the various embodiments described permit attachment to and transcription of RNA molecules and furthermore, may also have attached to them a reporter moiety useful in the detection and purification of the transcribed RNA. One of skill in the art would recognize that modified forms and functional analog nucleobases are also specifically contemplated.

The term "nucleoside" and "nucleotide" refers to a compound having a pyrimidine nucleobase, for example cytosine (C), uracil (U), or thymine (T), or a purine nucleobase, for example adenine (A) or guanine (G), linked to the C-1' carbon of a "natural sugar" (i.e., -ribose, 2'-deoxyribose, and the like) or sugar analogues thereof, including 2'-deoxy and 2'-hydroxyl forms. Typically, when the nucleobase is C, U or T, the pentose sugar is attached to the N$^1$-position of the nucleobase. When the nucleobase is A or G, the ribose sugar is attached to the N$^9$-position of the nucleobase (Kornberg and Baker, *DNA Replication*, 2$^{nd}$ Ed., Freeman, San Francisco, Calif., (1992)). The term "nucleotide" as used herein refers to a phosphate ester of a nucleoside as a monomer unit or within a polynucleotide, e.g., triphosphate esters, wherein the most common site of esterification is the hydroxyl group attached at the C-5' position of the ribose.

"Nucleoside analog" and "nucleotide analog" refer to compounds having modified nucleobase moieties (e.g., pyrimidine nucleobase analogs and purine nucleobase analogs described below), modified sugar moieties, and/or modified phosphate ester moieties (e.g., see Scheit, Nucleoside Analogs, John Wiley and Sons, (1980); F. Eckstein, Ed., Oligonucleotides and Analogs, Chapters 8 and 9, IRL Press, (1991)). The ribose or ribose analog may be substituted or unsubstituted. Substituted ribose sugars include, but are not limited to, those riboses in which one or more of the carbon atoms, such as the 2'-carbon atom or the 3'-carbon atom, can be substituted with one or more of the same or different substituents such as —R, —OR, —NRR or halogen (e.g., fluoro, chloro, bromo, or iodo), where each R group can be independently —H, C$_1$-C$_6$ alkyl or C$_3$-C$_{14}$ aryl. Particularly, riboses are ribose, 2'-deoxyribose, 2',3'-dideoxyribose, 3'-haloribose (such as 3'-fluororibose or 3'-chlororibose) and 3'-alkylribose, arabinose, 2'-O-methyl ribose, and locked nucleoside analogs (e.g., WO 99/14226), although many other analogs are also known in the art.

The term "nucleic acid" as used herein can refer to the nucleic acid material itself and is not restricted to sequence information (i.e. the succession of letters chosen among the five base letters A, C, G, T, or U) that biochemically characterizes a specific nucleic acid, for example, a DNA or RNA molecule. Nucleic acids described herein are presented in a 5'→3' orientation unless otherwise indicated.

As used herein, the term "reporter moiety" refers to a moiety that can be directly or indirectly detected. Detectable reporters include, but are not limited to affinity tags (e.g., biotin, avidin, streptavidin, etc.) and epitope tags recognized by an antibody. As used herein an "indirectly detectable" reporter necessitates interaction or reaction with either another substrate or reagent for detection. Indirectly detectable reporters include, but are not limited to affinity tags (needs affinity partner), eptiope tags (needs antibody), and enzyme substrate (needs enzyme).

As used herein, the phrase "wherein a reporter moiety is attached to said linker" means that the reporter moiety is attached to the linker attached to the nucleobase of the nucleotide analog. For example, a reporter moiety appended to the nucleobase via an aminoallyl group or other linking group attached to the nucleobase is "linked to the nucleobase." Linkers useful according to the invention are described herein below.

As used herein, the term "sugar analog" refers to analogs of the sugar ribose. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently —H, (C$_1$-C$_6$) alkyl or (C$_1$-C$_{14}$) aryl. Examples of substituted furanoses having 5 ring atoms include but are not limited to 2'-deoxyribose, 2'-(C$_1$-C$_6$)alkylribose, 2'-(C$_1$-C$_6$)alkoxyribose, 2'-(C$_5$-C$_{14}$)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C$_1$-C$_6$)alkylribose, 2'-deoxy-3'-(C$_1$-C$_6$)alkoxyribose, 2'-deoxy-3'-(C$_5$-C$_{14}$)aryloxyribose, 3'-(C$_1$-C$_6$)alkylribose-5'-triphosphate, 2'-deoxy-3'-(C$_1$-C$_6$)alkylribose-5'-triphosphate, 2'-deoxy-3'-(C$_1$-C$_6$)alkoxyribose-5'-triphosphate, 2'-deoxy-3'-(C$_5$-C$_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate. Further sugar analogs also include so called locked nucleic acids (LNAs) having the structure

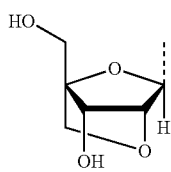

and those described in Wengel, et al. WO 99/14226, incorporated herein by reference.

The term "purine nucleobase" refers to a compound comprising a purine ring. It will be understood that a purine nucleobase can be any naturally occurring purine nucleobase known in the art, including but not limited to, adenine and guanine. The term "purine nucleobase analog" refers to natural, synthetic or derivative chemical compounds structurally similar to a naturally occurring purine in structure and/or function and is capable of forming a covalent bond to a sugar or sugar analog. Examples of purine nucleobase analogs (in the form of nucleobases, nucleosides or nucleotides), for which preparatory methods or commercial sources can be identified and can be found by suitable structure searching in available databases such as Chem. Abstracts Service (CAS), SciFinder, and the like.

The term "pyrimidine nucleobase" refers to a compound comprising a pyrimidine ring. It will be understood that a pyrimidine nucleobase can be any naturally occurring pyrimidine nucleobase known in the art, including but not limited to, uracil, thymine and cytosine. The term "pyrimidine nucleobase analog" refers to natural, synthetic or derivative heterocyclic compounds comprising at least one ring nitrogen atom capable of forming a covalent bond to a sugar or sugar analog.

Examples of pyrimidine nucleobase analogs (in the form of nucleobases, nucleosides or nucleotides), for which preparatory methods or commercial sources can be identified and can be found by suitable structure searching in available databases such as Chem. Abstracts Service (CAS), SciFinder, and the like, include but are not limited to the following exemplary structures:

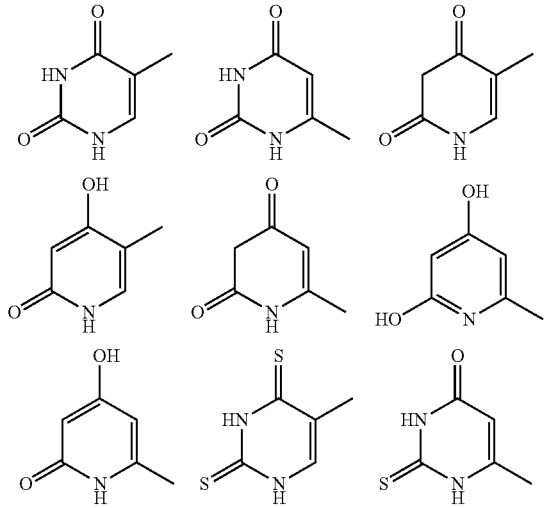

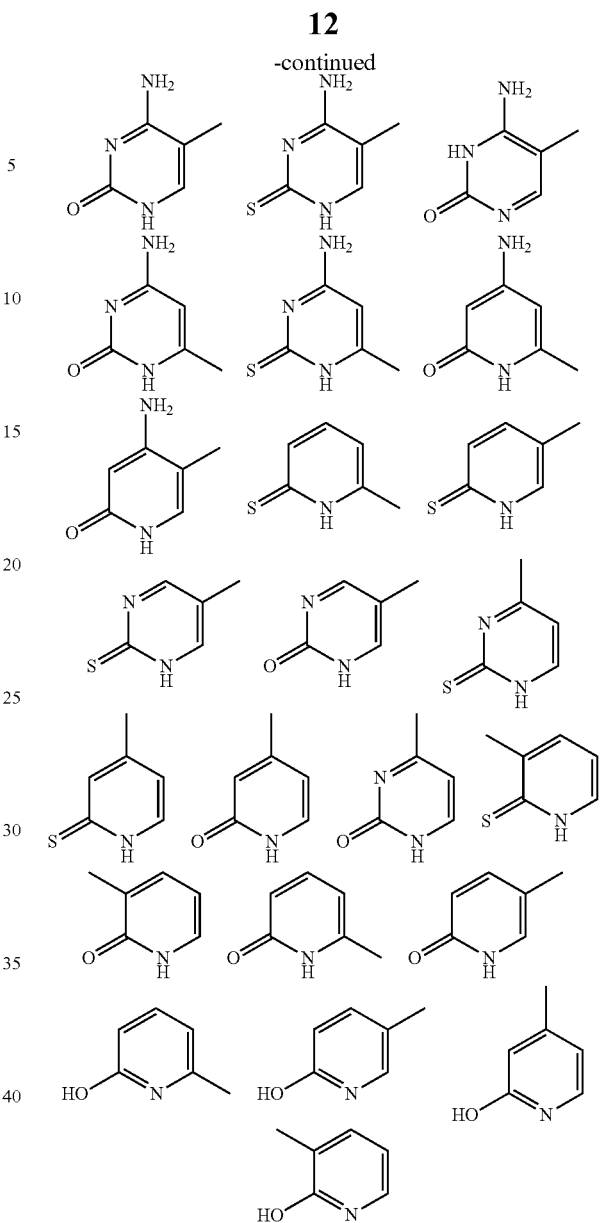

As used herein, the term "polynucleotide" refers to polymers of natural nucleotide monomers or analogs thereof, including double and single stranded deoxyribonucleotides, ribonucleotides, α-anomeric forms thereof, and the like. The terms "polynucleotide", "oligonucleotide" and "nucleic acid" are used interchangeably. Usually the nucleoside monomers are linked by internucleotide phosphodiester linkages, where as used herein, the term "phosphodiester linkage" refers to phosphodiester bonds or bonds including phosphate analogs thereof, and include associated counterions, including but not limited to $H^+$, $NH_4^+$, $NR_4^+$, $Na^+$, if such counterions are present. A polynucleotide may be composed entirely of deoxyribonucleotides, entirely of ribonucleotides or chimeric mixtures thereof.

As used herein, the term "terminator" means an enzymatically incorporatable nucleotide which prevents subsequent incorporation of nucleotides to the resulting polynucleotide chain and thereby halts polymerase-mediated extension. Typical terminators lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'- dideoxy-3'-fluororibose, for example. Alternatively, a ribofuranose analog can be used, such as 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (see, for example, Chidgeavadze et al., Nucleic Acids Res., 12:1671-1686 (1984), and Chidgeavadze et al. FEB. Lett., 183:275-278 (1985)). Nucleotide terminators also include reversible nucleotide terminators (Metzker et al. Nucleic Acids Res., 22(20):4259 (1994)).

As used herein, the term "nonextendable" or "3' nonextendable" refers to the fact that a terminator is incapable, or substantially incapable, of being extended in the 3' direction by a template-dependent DNA or RNA polymerase.

As used herein, the term "void" refers to the absence of a substituent group at the $R_3$ position of the cap analog. The lack of a substituent group results in no positive charge on the imidazole ring. In some embodiments the substituent group may be a $CH_3$ group. When the $CH_3$ group is present, there is a positive charge on the imidazole ring.

Reporter Moiety Labeled Dinucleotide Cap Analogs

Throughout this disclosure, various linkers and reporter moieties are presented. It should be understood that the illustrated linkers and reporter moieties are presented merely for convenience and brevity and should not be construed as an inflexible limitation of the scope of the embodiments claimed herein. Accordingly, the illustration of a labeled dinucleotide cap analog with a particular linker or reporter moiety is not limited to only the linker or reporter moiety so illustrated. For example, the illustrated linker could be replaced with an aminoallyl ($[—CH_2]_nCH_2NH_2$) where n=2-18, a secondary amine or an alkyl ($C_3$-$C_{10}$)$NH_2$ chain. Furthermore, the alkyl chain can comprise three to ten chain atoms with a terminal primary amine and the linker can be a cleavable or can be a non-cleavable linker. Likewise, the reporter moiety can be any moiety capable of binding to a substrate, for example, a magnetic bead, a chromatography column bound with, for example, avidin, streptavidin, antigen, antibody, and the like. The reporter moiety can be an affinity tag or an epitope tag. A reporter moiety such as biotin can be replaced with other affinity tags such as iminobiotin, avidin, and streptavidin. Non-limiting examples of biotin molecules that can comprise the reporter moiety include $C_5$-$C_{20}$-biotin, SS-biotin, XX-biotin, and NHS ester compounds thereof.

The novel dinucleotide cap analogs described herein are useful for, among other things, specifically transcribing the DNA of a molecule of interest to mRNA. The dinucleotide cap analog composition generally comprises:

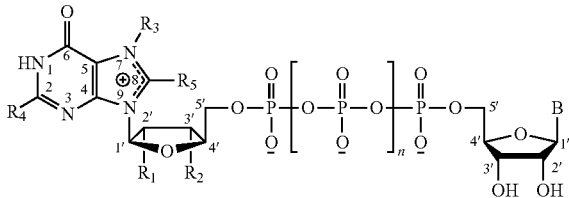

wherein: B is a nucleobase; $R_1$ is selected from a halogen, OH, and $OCH_3$; $R_2$ is selected from H, OH, and $OCH_3$; $R_3$ is $CH_3$ or void; $R_4$ is $NH_2$; $R_5$ is H; and n is 1, 2 or 3; wherein a linker is attached to one of $R_1$, $R_2$, $R_4$, $R_5$, or B.

As highlighted by the above structure, the carbon atoms are numbered differently. Specifically the carbon atom numberings include primes. The numbering system of the nucleobase heterocyclic rings lack a prime and the positions on the ribose are given a prime (').

The nucleobase can be a nucleobase or nucleobase analog that is operative in accordance with the various compositions and methods described herein. In some embodiments, the nucleobase can be a purine, purine analog, pyrimidine, pyrimidine analog and natural, synthetic and derivatives thereof. In some embodiments, the nucleobase can be adenine, adenine analogs and natural, synthetic and derivatives thereof. In some embodiments the nucleobase can be uracil, uracil analogs and natural, synthetic and derivatives thereof. In some embodiments, the nucleobase can be guanine, guanine analogs and natural, synthetic and derivatives thereof. In some embodiments, the nucleobase can be cytosine, cytosine analogs and natural, synthetic and derivatives thereof. In some embodiments, the nucleobase can be thymine, thymine analogs and natural, synthetic and derivatives thereof.

In various embodiments, the nucleobase is a purine, a 7-deazapurine, a pyrimidine, or a nucleobase analog. In some embodiments, the nucleobase is selected from the group comprising: adenine, cytosine, guanine, thymine, uracil, 7-deazapurines, 9-deazapurines, hypoxanthine, thizaolo[4,5-d]pyrimidines, pyrazolol[3,4-d]pyrimidine, pyrazin-2-ones, imidazol[1,5-a]1,3,5 trazinones, imidazo[4,5-d]pyrazines, 1,2,4-triazine, pryridazine, and 1,3,5 triazine.

In various embodiments the cap analog can also have novel substituent groups at the 2' and/or 3' positions of the ribose ring which also results in attaching of the cap on the RNA in the forward orientation. In some embodiments the attachment of fluorine or methoxy at the 2'-position ($R_1$) of the ribose ring has been shown to improve both capping efficiency and transcription efficiency. In some embodiments the attachment of methoxy or a deoxy substituent at the 3'-position ($R_2$) of the ribose ring has been shown to improve both capping efficiency and transcription efficiency. In some embodiments the N7-position of the guanine is methylated. FIG. 1 provides an example of the general structure of a biotin-labeled mCAP analog, $m^7G[5']pppp[5']U$—S—S-Biotin. As evidenced by FIG. 1, the dinucleotide cap analog has the capability to attach to an RNA transcript and have attached to the cap, for example, a biotin reporter moiety to use in isolation of the resulting capped transcript. In various embodiments, the N7-position on the guanine nucleotide is methylated, the $R_2$ position can be hydroxyl, methoxy or deoxy and n=2 such that the triphosphodiester bond of the Biotin-11-UTP is coupled to the Imidizolide $m^7GMP$.

The linker can encompasses any modifying group added to the dinucleotide cap that is operative in accordance with the various compositions and methods described herein. In various embodiments the linker is a chemical entity or entities which provide conjugation between the dinucleotide cap and the reporter moiety. In some embodiments the linker can have a first end connected to the dinucleotide cap and a primary amine second end which connects to the reporter moiety having an NHS ester form. In some embodiments the linker can be attached to the nucleobase at the N-4 or C-5 position of the nucleobase when the nucleobase is a pyrimidine, or at the C-2, C-6, or C-8 position of a purine nucleobase. In the case of a modification at the C-2, C-6 or C-8 position, the linker is an N. In some embodiments the linker can be attached to the C-2' or C-3' position of the pentose ring. When attached to the C-2' or C-3' position, the modification is the replacement of the —OH group to an O, an S, an N and so on, atom.

Figure 2:
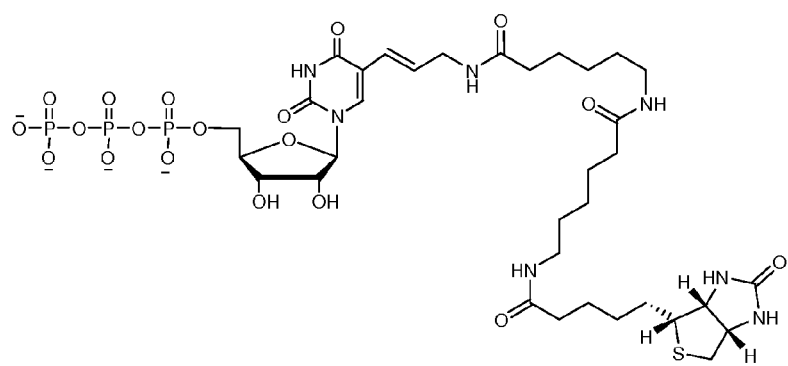
FIG. 2 provides examples of dinucleotide cap analogs with non-cleavable linkers attached to the affinity tag biotin.
Figure 2:
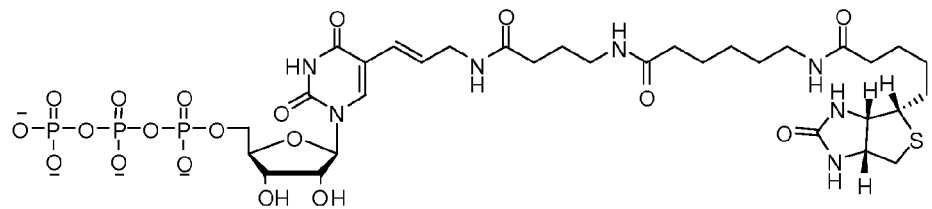
Figure 2:
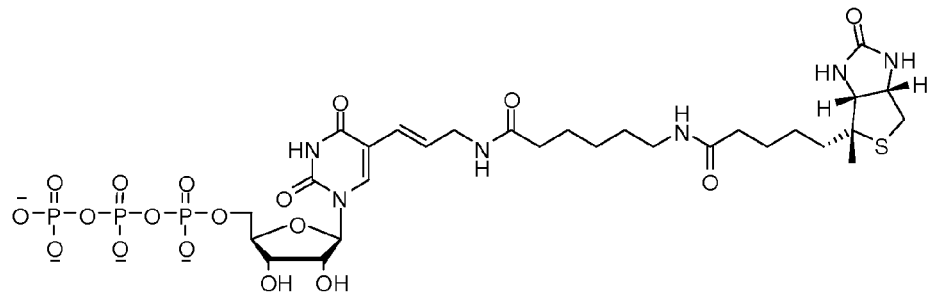
Figure 3:
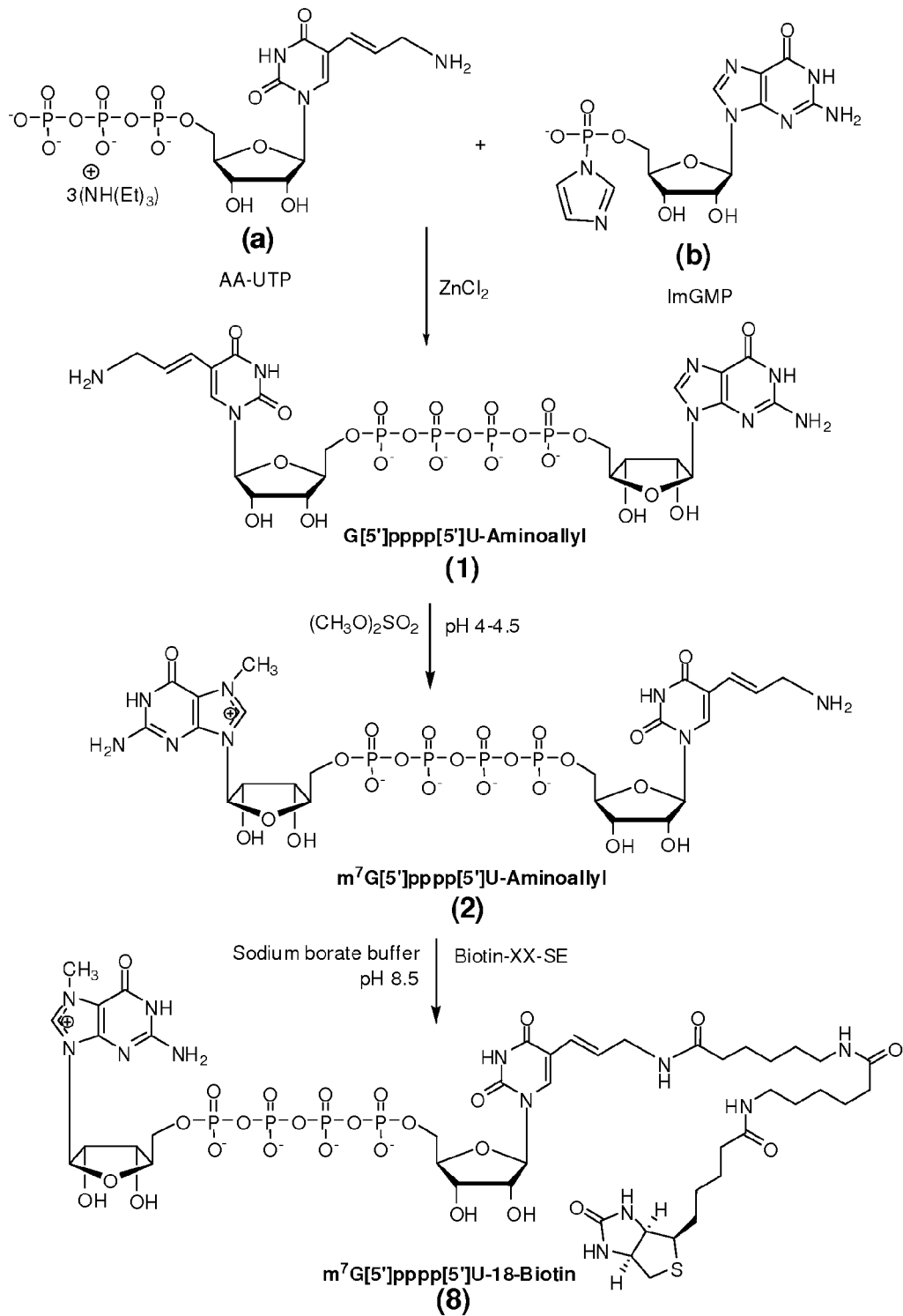
FIG. 3 provides the synthesis of $m^7G[5']pppp[5']U$-18-biotin with a non-cleavable linker.

In some embodiments useful linkers include, but are not limited to N, S, and O, an aminoallyl ($[—CH_2]_nCH_2NH_2$) where n=2-18, a secondary amine and an alkyl ($C_3$-$C_{10}$)$NH_2$ chain. Linkers can include, for example, an alkyl, allyl, or alkynyl amine modifying group attached to the nucleobase. As an alternative, linkers can include one or more ethylene oxy moieties. In some embodiments linkers can be cleavable or non-cleavable. In some embodiments non-cleavable linker examples include, but are not limited to $C_3$ to $C_{10}$ atom chain molecules, aminoallyl and the like. In some embodiments FIG. 2 provides an example of non-cleavable linkers with biotin as an affinity tag. FIG. 3 illustrates the synthesis of m$^7$G[5']pppp[5']U-18-biotin with a non-cleavable linker.

Figure 4:
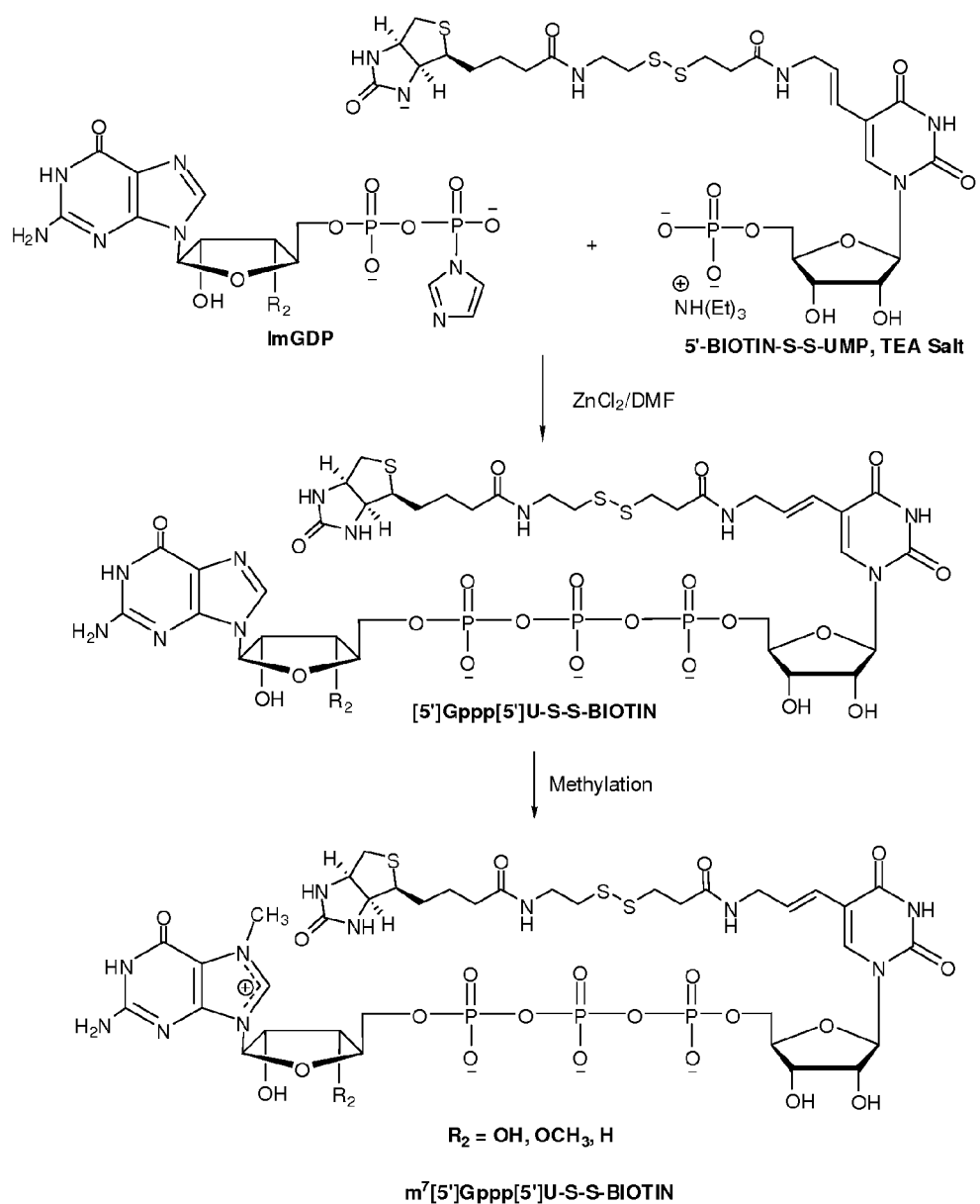
FIG. 4 provides the synthesis of $m^7G[5']pppp[5']U$—S—S-biotin with a cleavable linker.
Figure 5:
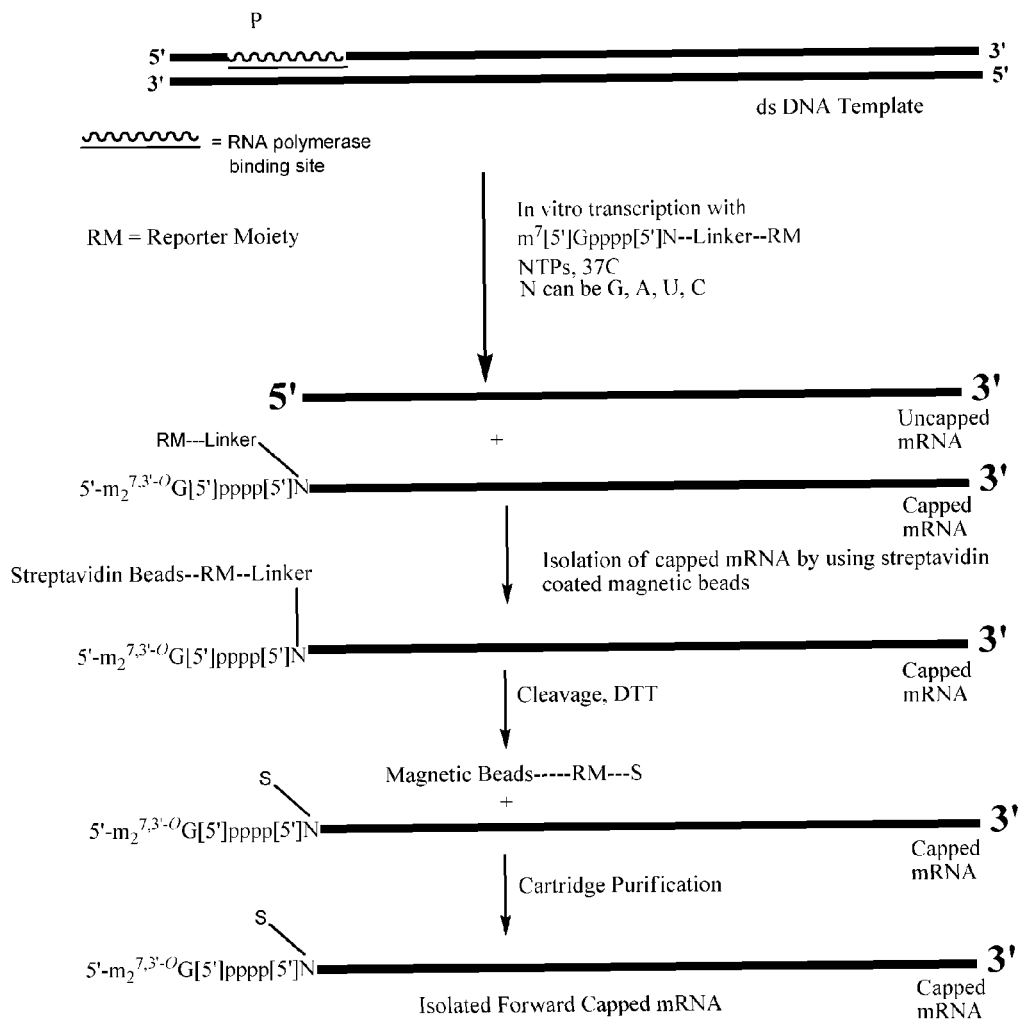
FIG. 5 provides a scheme for the preparation of 5' capped/biotin mRNA pre-transcription.
Figure 6:
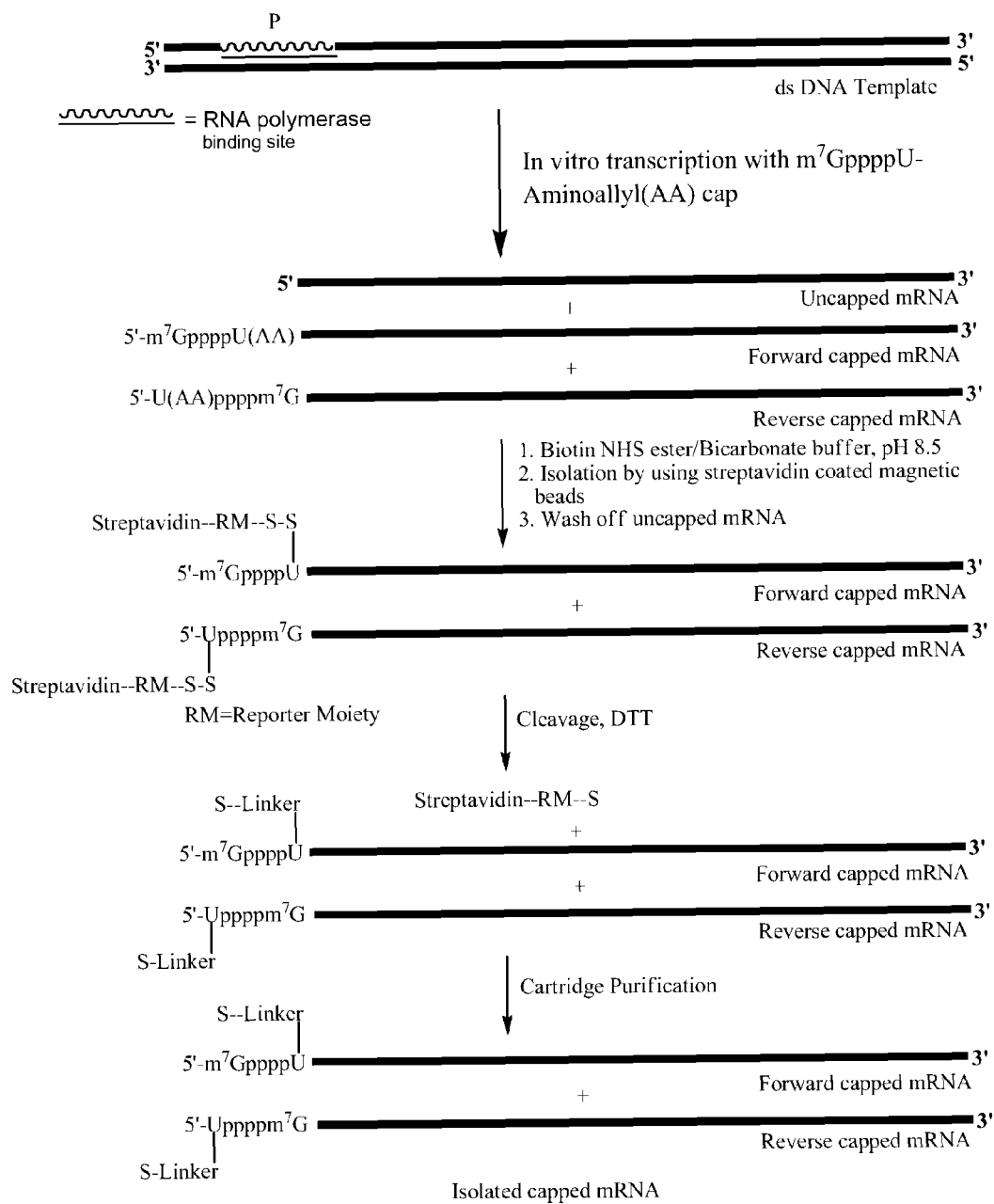
FIG. 6 provides a scheme for attaching the biotin tag to the cap analog following transcription and the subsequent isolation of 5' capped mRNA transcript.
Figure 7:
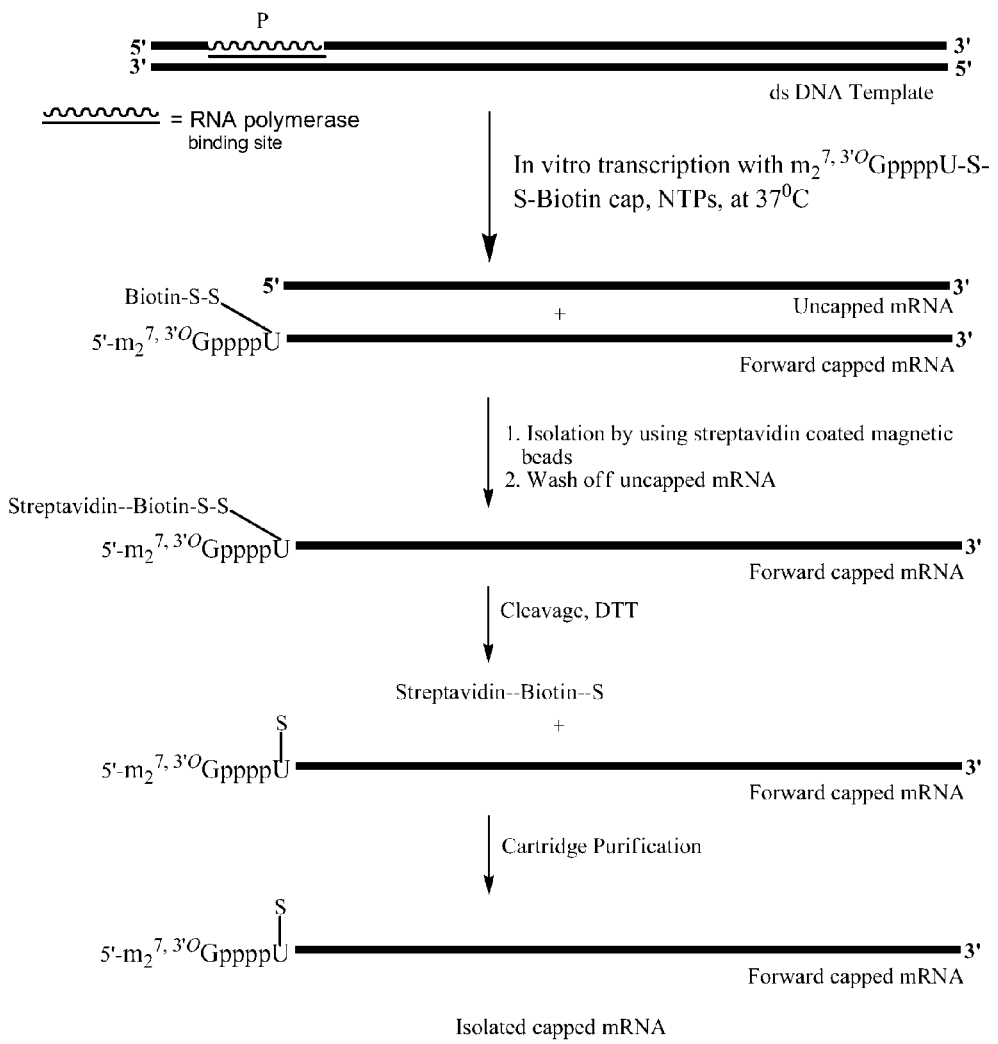
FIG. 7 provides a scheme for the preparation of 5' capped/biotin mRNA with an ARCA cap analog, pre-transcription.
Figure 8:
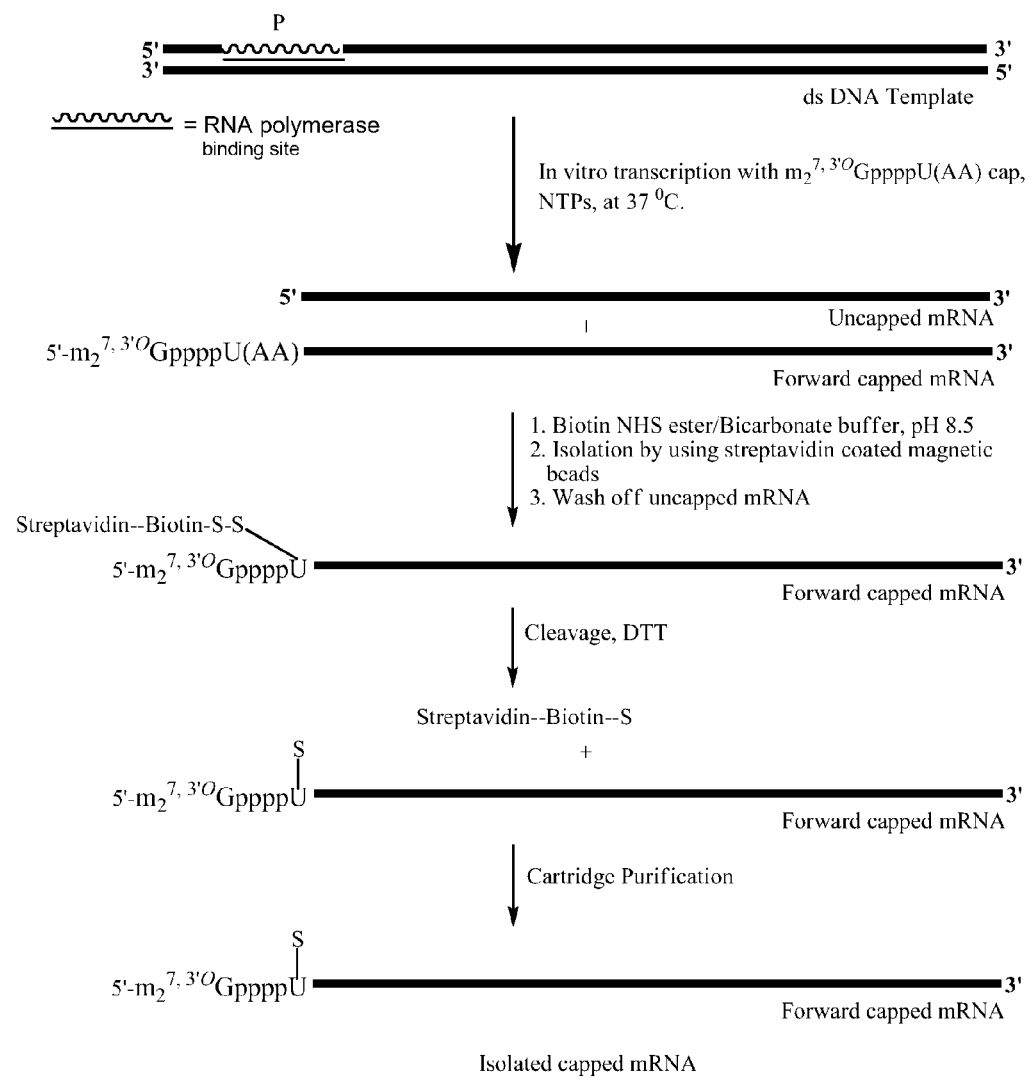
FIG. 8 provides a scheme for the preparation and isolation of 5' capped mRNA with an ARCA cap analog, post-translation.

In some embodiments examples of cleavable linkers include, but are not limited to, disulfide bonds. The disulfide bond (S—S) can be cleaved under mild reducing agents such as 50 mM dithiothreitol (DTT), or Tris(2-carboxyethyl)phosphine hydrochloride, (TCEP), or 100 mM 2-Mercaptoethanol, and or 1% Sodium borohydride (Shimkus, M., et al. *Proc. Natl. Acad. Sci. USA* 82, 2593-2597, (1985), Dawson, B. A., et al. *J. Biol. Chem.* 264(22), 12830-12837 (1989), Kirkley, T. L., *Anal. Biochem.*, 180, 231-236 (1989), Andrews, P. C., Dixon, J. E., *Anal. Biochem.*, 161, 524-528 (1987), Schonberg, A., *Chem. Ber.*, 163-164 (1935), Rauhut, M., et. al., *JACS*, 81, 1103-1107 (1959)). FIG. 4 illustrates the synthesis of m$^7$G[5']pppp[5']U—S—S-biotin which comprises a disulfide cleavable linker.

The reporter moiety can encompasses any detectable group added to the linker who is attached to the dinucleotide cap that is operative in accordance with the various compositions and methods described herein. In some embodiments the reporter moiety can be any moiety capable of binding to a substrate. In some embodiments the reporter moiety can be selected from an affinity tag and an epitope tag recognized by an antibody. In some embodiments, examples of moieties used in the isolation of capped RNA include, but are not limited to a magnetic bead coated with an affinity tag, a chromatography column bound with, for example, avidin, streptavidin, antigen, antibody, and the like. In some embodiments, the affinity tag can be selected from biotin, iminobiotin, avidin, and streptavidin. Non-limiting examples of biotin molecules that can comprise the reporter moiety include $C_5$-$C_{20}$-biotin, SS-biotin, XX-biotin, and NHS ester compounds thereof. The attachment of biotin reporter moieties and the NHS esters thereof is facilitated by the presence of a primary amine within the nucleobase at the 2' or 3' position which is modified on the pentose ring. The length of the linker arm varies, between at least a $C_4$-$C_{15}$ chain length depending upon the application.

In order to improve capping efficiency, the resulting transcription yield and the subsequent translation of the transcribed protein, the present application teaches chemically convenient and reproducible methods for the synthesis of modified cap analogs which can be isolated and purified following transcription of the mRNA and methods to use the purified, capped mRNAs in transfection, translation, protein identification, therapeutic and disease diagnostic and prognostic applications.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of Remington's Pharmaceutical Sciences (Maack Publishing, Easton Pa.). Such compositions may consist of novel cap analogs, antibodies to novel cap analogs, and mimetics, agonists, antagonists, or inhibitors of novel cap analogs.

In various embodiments, the compositions described herein, such as pharmaceutical compositions, may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

The design and synthesis of novel cap analogs such as m$^{7[5']}$Gpppp[5']U-18-Biotin with a non-cleavable linker (FIG. 2) and m7[5']Gppp[5']U—S—S-Biotin with a cleavable linker (FIG. 4), in which various moieties at the 2' and 3' positions on the ribose ring have been substituted are presented. Each reporter moiety labeled RNA cap analog finds utility in isolation of the capped transcript and in subsequent transfection, therapeutics, diagnostics, prognostics, or protein translation experiments.

Structures were confirmed by $^1$H NMR and $^{31}$P NMR. Transcripts produced with T7 RNA polymerases using "anti-reverse" cap analogs (ARCAs), with a linker or a linker plus a biotin reporter moiety were of the predicted length and indistinguishable in size and homogeneity from those produced with m$^7$GppppG.

Therapeutic & Diagnostic Applications of Novel Cap Analogs

In more recent years, the use of capped RNA for therapeutic purposes has been studied. Mainly it has the potential to be used to generate vaccines against infectious diseases or cancers (Sullenger and Gilboa, *Nature*, 418, 252-258, (2002). Capped RNA is used to produce non-infectious particles of Venezuelan Equine Encephalitis virus containing an RNA encoding immunogen. These non-replicating viral particles are injected into humans where they can enter host cells. Once in the host cell, the viral particles dissociate and the mRNA encoding the immunogen is translated into protein. These proteins can induce an immune response. These types of vaccines are in development for human immunodeficiency virus (HIV), feline immunodeficiency virus, human papilloma virus type 16, tumors, lassa virus, Ebola virus, Marburg virus, anthrax toxin from *Bacillus anthraces*, and botulinum toxin (Burkhead et al., *Vaccine*, 21(3-4), 258-268, (2002); Davis et al., *IUBMB Life*, 53(4-5), 209-211 (2002); Eiben et al., *Cancer Res.*, 62(20), 5792-5799 (2002); Hevey et al., *Virology*, 251(1), 28-37, (1998); Pushko et al., *J. Virol.*, 75, 11677-11685, (2001); Pushko et al., *Virology* 239, 389-401, (1997); Lee et al., *Infect. Immun.*, 69, 5709-5715, (2001); Lee et al., *Infect Immun.*, 71, 1491-1496, (2003)).

These vaccine strategies will require large quantities of capped RNA. Developing methods to synthesize and purify capped RNA will be important to make these vaccines commercially feasible. As well, strategies to increase the percentage of full length capped RNA in a transcription reaction leading to a more homogenous product will be preferred in the vaccine industry as highly pure components are usually required for human use. In addition, researchers prefer to use products that are as pure as possible to minimize the number of variables in an experiment. As well, the purer the product, the more potent it is. Current protocols, enabling the production of about 1 mg/mL of capped RNA, are simply insufficient for the scale of production needed for these applications (Frank Grunebach et al *Cancer Immunol. Immunother.*, 54, 517-525, (2005); Sullenger and Gilboa, *Nature*, 418, 252-258, (2002).

Another approach in use is to isolate dendritic cells from a patient and then to transfect the dendritic cells with capped RNA encoding immunogen. The dendritic cells translate the capped RNA into at least one protein that induces an immune response against this protein. In a small human study, immunotherapy with dendritic cells loaded with CEA capped RNA was shown to be safe and feasible for pancreatic cancer patients (Morse et al. *Int. J. Gastrointest. Cancer*, 32:1-6, (2002)). It was also noted that introducing at least one single capped RNA species into immature dendritic cells induced a specific T-cell response (Heiser et al. *J. Clin. Invest.*, 109:409-417, 2002).

Those having ordinary skill in the art will understand that many modifications, alternatives, and equivalents are possible. All such modifications, alternatives, and equivalents are intended to be encompassed herein.

MATERIALS AND METHODS

Reagents

All of the reagents and solvents are used as such without further purification, unless otherwise stated. Guanosine 5'-diphosphate, Dimethyl sulfate, anhydrous dimethylformamide, 2,2'-dithiodipyridine (Aldrithiol), Triphenylphosphine, trimethylphosphate ($(OMe)_3P$), phosphorous oxychloride, phosphorous pentoxide, orthophosphoric acid, anhydrous methylene chloride, dichloromethane, Tributylamine, and anhydrous pyridine were purchased from Sigma-Aldrich Co. 3'-O-Me-Guanosine is available from Chemgene, Boston, Mass. Imidazolide GMP, Imidazolide GDP, Imidazolide 2'F-GMP, Imidazolide 3'$CF_3$-GDP, Imidazolide $m^7$GMP, 1M tris (triethylammonium)phosphate, and tributylammonium orthophosphate were made as taught herein or in A. Kore, and G. Parmar, *Synthetic Comm.*, 36:3393-3399, (2006), incorporated herein by reference in its entirety. Allylamine UTP (AA-UTP) and UTP TEA were obtained from Ambion Inc., an Applied Biosystems business, Austin, Tex.

Ezlink-Sulfo-NHS S—S biotin and Ezlink-Sulfo-NHS LC-LC biotin were from Pierce (Rockford, Ill.). Biotin-XX, SE, Biotin-12, SE, and Biotin-X, SE used to make Bio-18-UTP, Bio-16-UTP and Bio-11-UTP, respectively, were from Biotium (Hayward, Calif.).

The cap analogs were analyzed by $^1$H NMR and $^{31}$P NMR (Bruker Avance), $^1$H was collected at 400.1446006 MHz by using $D_2O$ solvent and the $^{31}$P was collected at 161.9968531 MHz by using $D_2O$ solvent. Mass Spectroscopy was performed on an Applied Biosystems/Sciex, MDX API 150 model and MALDI-TOF was performed on an Applied Biosystems, Voyager DE-PRO model. Analytical HPLC was performed on a Waters, Alliance instrument using Hypersil SAX columns, 5 μm, 250 mm×4.6 mm (Alltech Associates Inc. Deerfield, Ill.).

EXAMPLES

Synthesis of a dinucleotide cap analog is disclosed in US patent application 2005/0287539, incorporated herein by reference. The synthesis of novel cap analog compositions which improve capping efficiency and yield of transcribed RNA have been described in PCT patent application WO 07 15896, incorporated herein by reference. Such capped RNA analogs have been shown to improve transcription and translation efficiency.

Aspects of the present teachings may be further understood in light of the following examples, which should not be construed as limiting the scope of the present teachings in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Example 1

Synthesis of 7-Methyl Guanosine 5'-diphosphate

In a clean, dry 2000 mL round bottom flask equipped with a stifling bar and under a stream of argon slowly dissolve dry and finely powdered guanosine 5'-diphosphate (1), (10.0 g, 20.5 mmol), either in free acid or sodium as a counter ion form, in 200 mL water, adjusting pH to 4.0 with glacial acetic acid. Dimethyl sulfate (20 mL, 119.04 mmol) was then added over a period of one hour with constant stirring at room temperature and the reaction continued for an additional hour during which time a decrease in pH was observed but pH was kept between pH 3.8 to 4.0 by drop-wise addition of 10 mM NaOH and methylation was monitored by analytical HPLC for progress. Methylation was determined to be 98% complete within 2 hr. After 2 hr, the reaction mixture was extracted with $CHCl_3$ (3×200 mL) to remove unreacted excess dimethyl sulfate.

The resulting aqueous layer was further evaporated on a rotary evaporator to remove any chloroform traces, and then further diluted to 1.5 L with water and loaded on an anion exchange resin, i.e., DEAE Sepharosa fast flow packed in a BPG 100 column (Amersham GE, Piscataway, N.J., USA). BPG (biological process glass) 100 specification: 100/500 column (100 mm in diameter and 50 cm in height), packed with DEAE Sepharosa fast flow resin to the bed volume of 400 mm. The desired compound was eluted by using four bed volumes of gradient from 0 to 80% of 1 M TEAB buffer (triethylammonium bicarbonate), pH 7.5, at a flow rate of 100 mL/min, using AKTA purifier 100 FPLC (Amersham GE). At 45% TEAB buffer, 7-methylguanosine 5'-diphosphate ($m^7$GDP) was eluted as a large broad peak, with a strong ultraviolet absorbance at 254 nm. The residual bicarbonate was removed by co-evaporating with methanol, 3×600 mL. The resulting residue was transferred to a centrifuge tube, and 8.9 g sodium perchlorate dissolved in 1.1 L acetone was added and cooled 2 hr at 4° C. The resulting mixture was centrifuged and the supernatant liquid was discarded. The precipitate was ground with a new portion of acetone, cooled and centrifuged, repeating once. The precipitate was dried in a vacuum desiccator over $P_2O_5$. The resulting amorphous white powder was 7 methyl-guanosine 5'-diphosphate. Taken from Kore, A. and Parmar, G. Nucleosides, Nucleotides, and Nucleic Acids, 25:337-340, 2006, incorporated herein by reference in its entirety.

Example 2

Synthesis of Nucleoside-5'-diphosphates

Although the following procedure illustrates synthesis of guanosine-5'-diphosphate, one of skill in the art would be able to use the procedure for the synthesis of adenosine-5'-diphosphate, uridine-5'-diphosphate, and cytidine-5'-diphosphate, and analogs and derivatives thereof. In a clean, dry 500 mL round bottom flask equipped with a stifling bar the triethylammonium salt of guanosine 5'-monophosphate (10.0 g, 21.5 mmol) in anhydrous dimethylformamide (200 mL) was stirred together, triethylamine was added (2.4 mL, 142.8 mmol) and allowed to stir for 5 min, followed by the addition of Imidazole (5.86 g, 86.1 mmol), 2,2'-dithiodipyridine (7.4 g, 33.58 mmol), and triphenylphosphine (8.9 g, 33.9 mmol). Stirring was continued for 2 hr at room temperature. The reaction was allowed to go to completion as determined by HPLC and then poured slowly into a mixture of sodium perchlorate (7 g) in acetone (1500 mL), and then cooled for 30 min at 4° C. The reaction mixture was centrifuged, discarding the supernatant. Traces of imidazole and triphenylphosphine were removed by grinding the solid with a new portion of acetone (400 mL), cooling and again centrifuged, repeating once. The precipitate was dried in a vacuum oven over $P_2O_5$ at 24° C. (30 mbar pressure). The ribonucleoside-5'-phosphoroimidazolide thus obtained was dissolved in dimethylforamide (200 mL), and a 1 M solution of tributylammonium orthophosphate in dimethylformamide (80 mL) was added drop-wise to the vigorously stirred mixture over a period of 30 min Zinc chloride (2 g, 14.67 mmol) was added and the reaction mixture stirred at room temperature for 3 hr. Completion of the reaction was monitored by HPLC. The reaction mixture was quenched with water (50 mL) and extracted with chloroform (3×200 mL), concentrated in a rotary evaporator and then purified by application to an anion exchange resin.

Purification by column chromatography was accomplished with a DEAE Sepharose fast flow resin packed in an XK 50/60 column (50 mm diameter and 60 cm long) (Amersham GE). The desired compound was eluted by using four bed volumes of gradient from 0 to 80% of 1 M TEAB buffer pH 7.5 (triethylammonium bicarbonate) at a flow rate of 20 mL/min, using an AKTA purifier 100 FPLC (Amersham GE). At 55% TEAB buffer, the desired product (nucleoside-5'-diphosphate) was eluted as a large broad peak, with a strong ultraviolet absorbance at 254 nm. The nucleoside-5'-diphosphate-containing fractions were pooled and evaporated using a rotary evaporator to give triethylamine salt of the desired diphosphate compound. Taken from A. Kore, and G. Parmar, Synthetic Comm., (2006) supra.

Example 3

Synthesis of 3'-O-Methyl Guanosine Monophosphate (3'-O-Me-GMP) TEA Salt

In a clean, dry 500 mL round bottom flask equipped with a stifling bar and under a stream of argon slowly add dry and finely powdered 3'-O-Me-Guanosine, (6 g, 20 mmol) to a mixture of trimethylphosphate ((OMe)$_3$P) (50 mL) and phosphorous oxychloride (POCl$_3$) (6 mL, 60 mmol) at 0° C. in small portions with continuous stifling under argon. The mixture was kept at 0-4° C. and allowed to stir at least 19 hrs. Diethyl ether (200 mL) was added to extract the excess phosphorous oxychloride and to simultaneously precipitate the 3'-O-methylguanosine-5'-phosphodichloridate, which was then pelleted by centrifugation and dissolved in 100 mL ice-cold 5% NaHCO$_3$ in water. The resulting aqueous solution was adjusted to pH ~1.5 using 1 N NaOH. After stifling at 0-4° C. for an additional 20 hr, the pH was adjusted to 7.0 and the resulting mixture was applied to a column of DEAE Sephadex A25. The column was washed with 5 mmol TEAB buffer, pH 7.5 and then eluted with freshly prepared 1M Triethylammonium bicarbonate (TEAB) buffer, pH 7.5. Fractions containing the 3'-O-Me GMP TEA salt were pooled, concentrated to dryness.

Example 4

Synthesis of Imidazolyl GMP

Commercially available disodium salt of GMP was passed through a DEAE Sepahadex column and eluted with ammonium bicarbonate buffer (pH 7.5) to obtain the triethylamine (TEA) salt of GMP. To a dried TEA salt of GMP (4.0 g, 7.1 mmol) was added aldrithiol (3.13 g, 14.19 mmol), imidazole (2.42 g, 35.49 mmol), triphenylphosphine (3.72 g, 14.19 mmol) and 50 mL of anhydrous DMF. To this solution was added 1.09 mL (7.81 mmol) of triethylamine and the solution was stirred overnight. 10 µL of 20 times diluted reaction solution was injected into a Waters HPLC (Hypersil SAX Column, 5 µm, 250×4.6 mm, Buffer A: 50 mmol Ammonium Phosphate Monobasic, pH 2.8; Buffer B: 750 mmol Ammonium Phosphate Monobasic, pH 3.7). The HPLC chromatogram showed the presence of a new peak corresponding to imidazolyl GMP and the absence of TEA GMP. The reaction mixture was centrifuged and the supernatant solution was collected and kept at 4° C. To a solution of 5 g of NaClO$_4$ in 500 mL of acetone maintained at −20° C. for 2 hr was added the supernatant solution to precipitate imidazolyl GMP (Im-GMP). The heterogeneous solution was centrifuged and the supernatant solution was discarded. The precipitate was washed with 3×200 mL of acetone to remove yellow colored impurities/byproducts and residual sodium perchlorate. Imidazolyl GMP (ImGMP) (3.5 g, 93.31%) was dried under vacuum over P$_2$O$_5$ for a few hours and immediately stored at −20° C.

Example 5

Synthesis of 3'-O-Me-GMP Imidazolide

In a clean, dry 1 L round bottom flask equipped with a stifling bar and under a stream of argon slowly add anhydrous DMF (144 mL) and the triethylamine (0.933 mL, 9.23 mmol) allow to stir for at least 5 min To this slowly was add the dry and finely powdered 3'-O-Me-GMP TEA salt, (3.5 g, 7.34 mmol) in small portions with continuous stifling under argon. Thereafter the Imidazole (2.05 g, 30.1 mmol), Aldrithiol (2.65 g, 12.02 mmol), and triphenylphosphine (3.13 g, 11.9 mmol) were added and the reaction allowed to stir at room temperature for at least 2-3 hr, during which the reactants became soluble making the reaction appear clear yellow colored. Upon completion, sodium perchlorate (3.0 g, 24.5 mmol) dissolved in acetone with continuous stirring and to this mixture, slowly added, was the reaction mixture. This mixture was then poured in two 1 L Nalgene bottles and cooled in a refrigerator at −80° C. for 30 minutes. The mixture was then subjected to centrifugation at 3000 rpm for 15 min and the supernatant was discarded. The precipitate was ground with a new portion of acetone and centrifuged. The process was repeated once more and the precipitate was dried in a vacuum desiccator over phosphorous pentoxide, yielding 3'-O-Me-GMP Imidazolide.

Example 6

Synthesis of 3'O-Me-GDP TEA Salt

Synthesis of Tris(triethylammonium)phosphate Linker

Anhydrous orthophosphoric acid (22.5 g, 229.59 mmol) was added to 50 mL of anhydrous methylene chloride in a clean, oven dried 250 mL flask equipped with a stirring bar. Tributylamine (54.6 mL, 229.6 mmol) was then added into the solution drop wise through an addition funnel over a period of 30 min The mixture was left stifling for 1 hr. CH$_2$Cl$_2$ was then evaporated and the reaction residue was co-evaporated with 3×30 mL of anhydrous pyridine and then 2×30 mL of anhydrous DMF. The Tris(triethylammonium) phosphate linker product was dissolved in 100 mL anhydrous DMF so as to have a final concentration of 1 M, and stored over 4 Å molecular sieves at 4° C.

In a clean, dry 1 L round bottom flask equipped with a stirring bar and under a stream of argon anhydrous DMF (40 mL) was slowly added and stirred for at least 5 minutes. To this was slowly added finely powdered 3'-O-Me-GMP Imidazolide (Ex. 5), (3.0 g, 7.04 mmol) in small portions with continuous stirring under argon. Zinc chloride (2.0 g, 14.67 mmol) was added in small portions until the contents were dissolved. Thereafter, the tris(triethylammonium) phosphate linker and 1 M tributylammonium orthophosphate (40 mL) was added slowly to the reaction mixture under argon and the reaction was allowed to stir at room temperature for 5 hr. The reaction when followed on HPLC showing complete conversion of the starting material, 3'-O-Me-GMP Imidazolide (Ex. 5) to its corresponding diphosphate. Upon completion, the reaction was supplemented with water, 100 mL, and the resultant mixture was extracted with chloroform (3×250 mL), subjected to volume reduction (~100 mL) by evaporation and applied to DEAE Sephadex A25 column, eluting with a linear gradient of freshly prepared 1 M TEAB, pH 7.5. The fractions containing the pure 3'O-Me-GDP TEA salt were eluted, combined and evaporated to dryness.

Example 7

Synthesis of $m_2^{7,3'O}$GDP

To a stirred solution of 3'-O-Me-GDP TEA salt (Ex. 6), (4.0 g, 6.1 mmol) in 100 mL of nuclease free water, concentrated glacial acetic acid was slowly added to adjust the pH of the solution to 4.0; dimethyl sulfate (($Me)_2SO_4$) (20 mL, 210 mmol) was slowly added drop wise over a period of 60 min, while maintaining the pH~4.0-4.5 with 50 mM NaOH. The reaction was allowed to stir at room temperature for 2 hr and methylation was monitored by HPLC. After 2 hr, the reaction mixture was extracted with $CHCl_3$ (3×250 mL) to remove unreacted dimethyl sulfate. The aqueous layer was applied to a DEAE Sephadex column and the fractions containing the product were pooled, evaporated and dried in a vacuum desiccator over phosphorous pentoxide to give m7-3'-O-Me GDP (N-7-Me-3'-O-GDP, $m_2^{7,3'O}$GDP) as a fine powder.

The examples disclosed herein for the synthesis of novel dinucleotide cap analogs illustrate the use of guanine and uracil nucleobases in the dinucleotide RNA cap. The examples describe illustrated cap analogs, however, there are additional cap analogs conceived which will also function in practicing the invention as illustrated. One of skill in the art will recognize that any nucleobase, nucleobase analog, rather natural, synthetic or a derivative thereof as well as any sugar or sugar analog or linker could be used and is contemplated herein.

Example 8

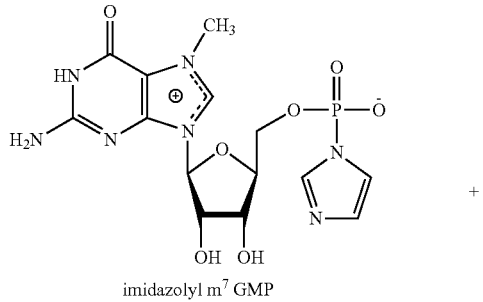

imidazolyl $m^7$ GMP

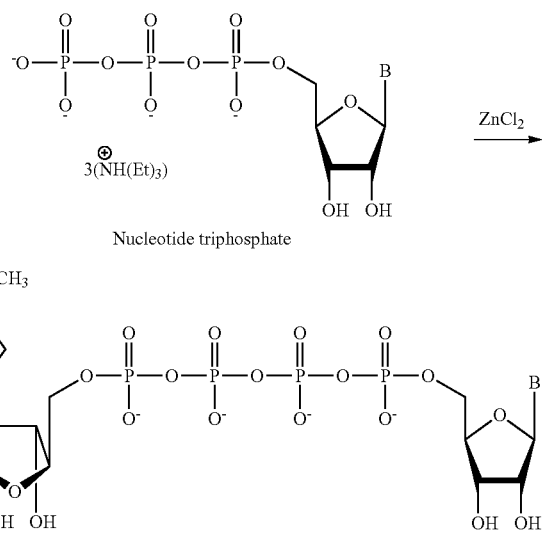

Nucleotide triphosphate

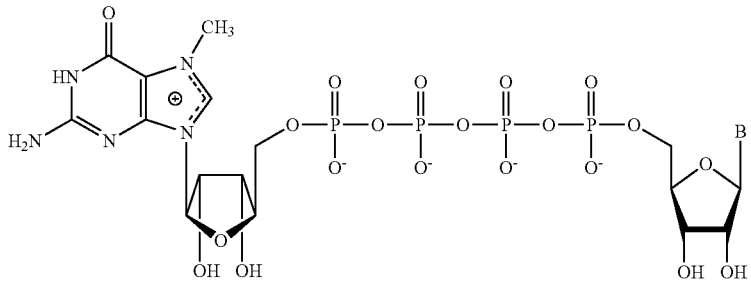

B can be any nucleobase and may have a linker.
Positions 2 and 8 of $m^7$Guanosine may also be modified with a linker.
Positions 2' and 3' of the guanosine ribose ring may also be modified with a linker.

The coupling reaction of imidazolyl $m^7$GMP with a corresponding nucleobase modified nucleotide in the presence of $ZnCl_2$ provides the corresponding cap analog as shown in the above scheme.

TABLE 1

Cap Analogs with Linkers (Nos. 1-6),
Linker + Reporter Moiety (Nos. 7-29),
Control Cap (No. 30)

| No | Abbreviation | $R_1$(2') | $R_2$(3') | $R_3$ | $R_4$ | $R_5$ | ARCA |
|---|---|---|---|---|---|---|---|
| 1 | G[5']pppp[5']U-Aminoallyl & G[5']pppp[5']C-Aminoallyl | OH | OH | void | $NH_2$ | H | No |
| 2 | $m^7$G[5']pppp[5']U-Aminoallyl & $m^7$G[5']pppp[5']C-Aminoallyl | OH | OH | $CH_3$ | $NH_2$ | H | Yes |
| 3 | $m_2^{7,3'O}$G[5']pppp[5']U-Aminoallyl & $m_2^{7,3'O}$G[5']pppp[5']C-Aminoallyl | OH | $OCH_3$ | $CH_3$ | $NH_2$ | H | Yes |
| 4 | $m_2^{7,2'O}$G[5']pppp[5']U-Aminoallyl & $m_2^{7,2'O}$G[5']pppp[5']C-Aminoallyl | $OCH_3$ | OH | $CH_3$ | $NH_2$ | H | Yes |
| 5 | $m^{7,2'F}$G[5']pppp[5']U-Aminoallyl & $m^{7,2'F}$G[5']pppp[5']C-Aminoallyl | F | OH | $CH_3$ | $NH_2$ | H | Yes |
| 6 | $m^7$3'dG[5']pppp[5']U-Aminoallyl & $m^7$3'dG[5']pppp[5']C-Aminoallyl | OH | H | $CH_3$ | $NH_2$ | H | Yes |

TABLE 1-continued

Cap Analogs with Linkers (Nos. 1-6),
Linker + Reporter Moiety (Nos. 7-29),
Control Cap (No. 30)

| No | Abbreviation | $R_1(2')$ | $R_2(3')$ | $R_3$ | $R_4$ | $R_5$ | ARCA |
|---|---|---|---|---|---|---|---|
| 7 | G[5']pppp[5']U-18-Biotin & G[5']pppp[5']C-18-Biotin | OH | OH | void | $NH_2$ | H | No |
| 8 | $m^7$G[5']pppp[5']Nuc-18-Biotin non cleavable linker | OH | OH | $CH_3$ | $NH_2$ | H | No |
| 9 | $m_2^{7,\,3'O}$G[5']pppp[5']Nuc-18-Biotin non cleavable linker | OH | $OCH_3$ | $CH_3$ | $NH_2$ | H | Yes |
| 10 | $m_2^{7,\,2'O}$G[5']pppp[5']Nuc-18-Biotin non cleavable linker | $OCH_3$ | OH | $CH_3$ | $NH_2$ | H | Yes |
| 11 | $m^{7,\,2'F}$G[5']pppp[5']Nuc-18-Biotin non cleavable linker | F | OH | $CH_3$ | $NH_2$ | H | Yes |
| 12 | $m^7$ 3'dG[5']pppp[5']Nuc-18-Biotin non cleavable linker | OH | H | $CH_3$ | $NH_2$ | H | Yes |
| 13 | $m^7$G[5']pppp[5']Nuc-S-S-Biotin disulfide cleavable linker | OH | OH | $CH_3$ | $NH_2$ | H | No |
| 14 | $m_2^{7,\,3'O}$G[5']pppp[5']Nuc-S-S-Biotin disulfide cleavable linker | OH | $OCH_3$ | $CH_3$ | $NH_2$ | H | Yes |
| 15 | $m_2^{7,\,2'O}$G[5']pppp[5']Nuc-S-S-Biotin disulfide cleavable linker | $OCH_3$ | OH | $CH_3$ | $NH_2$ | H | Yes |
| 16 | $m^{7,\,2'F}$G[5']pppp[5']Nuc-S-S-Biotin disulfide cleavable linker | F | OH | $CH_3$ | $NH_2$ | H | Yes |
| 17 | $m^7$ 3'dG[5']pppp[5']Nuc-S-S-Biotin disulfide cleavable linker | OH | H | $CH_3$ | $NH_2$ | H | Yes |
| 18 | $m^{7,\,8\text{-}S\text{-}S\text{-}Biotin}$G[5']pppp[5']Nuc | OH | OH | $CH_3$ | $NH_2$ | S-S-Biotin | No |
| 19 | $m_2^{7,\,3'O,\,8\text{-}S\text{-}S\text{-}Biotin}$G[5']pppp[5']Nuc | OH | $OCH_3$ | $CH_3$ | $NH_2$ | S-S-Biotin | Yes |
| 20 | $m_2^{7,\,2'O,\,8\text{-}S\text{-}S\text{-}Biotin}$G[5']pppp[5']Nuc | $OCH_3$ | OH | $CH_3$ | $NH_2$ | S-S-Biotin | Yes |
| 21 | $m_2^{7,\,2'F,\,8\text{-}S\text{-}S\text{-}Biotin}$G[5']pppp[5']Nuc | F | OH | $CH_3$ | $NH_2$ | S-S-Biotin | Yes |
| 22 | $m^{7,\,8\text{-}S\text{-}S\text{-}Biotin}$ 3'dG[5']pppp[5']Nuc | OH | H | $CH_3$ | $NH_2$ | S-S-Biotin | Yes |
| 23 | $m^{7,\,2\text{-}S\text{-}S\text{-}Biotin}$G[5']pppp[5']Nuc | OH | OH | $CH_3$ | S-S-Biotin | H | No |
| 24 | $m_2^{7,\,3'O,\,2\text{-}S\text{-}S\text{-}Biotin}$G[5']pppp[5']Nuc | OH | $OCH_3$ | $CH_3$ | S-S-Biotin | H | Yes |
| 25 | $m_2^{7,\,2'O,\,2\text{-}S\text{-}S\text{-}Biotin}$G[5']pppp[5']Nuc | $OCH_3$ | OH | $CH_3$ | S-S-Biotin | H | Yes |
| 26 | $m_2^{7,\,2'F,\,2\text{-}S\text{-}S\text{-}Biotin}$G[5']pppp[5']Nuc | F | OH | $CH_3$ | S-S-Biotin | H | Yes |
| 27 | $m^{7,\,2\text{-}S\text{-}S\text{-}Biotin}$ 3'dG[5']pppp[5']Nuc | OH | H | $CH_3$ | S-S-Biotin | H | Yes |
| 28 | $m^{7,\,2\text{-}S\text{-}S\text{-}Biotin}$G[5']pppp[5']Nuc | S-S-Biotin | OH | $CH_3$ | $NH_2$ | H | Yes |
| 29 | $m^{7,\,3'\text{-}S\text{-}S\text{-}Biotin}$G[5']pppp[5']Nuc | OH | S-S-Biotin | $CH_3$ | $NH_2$ | H | Yes |
| 30 | $m_2^{7,\,3'O}$G[5']pppp[5']U | OH | $OCH_3$ | $CH_3$ | $NH_2$ | H | Yes |
| 31 | Biotin-18-UTP | | | | | | n/a |

Nuc = Nucleobase,
G = guanine,
C = cytosine,
U = uracil;
UTP = uracil triphosphate Table 1 illustrates dinucleotide caps having modifications within at least one of the component structures comprising: the nucleobase and its substituents; the sugar moiety and its substituents; and the number of phosphate groups linking the nucleotides together. Additional modifications can comprise a linker, either cleavable or non-cleavable, and a reporter moiety. Although the reporter moiety indicated is biotin, it is not intended that the present teachings be limited to such an embodiment as other affinity tags can substitute for biotin. On the contrary, the present teachings encompass various alternatives, modifications, and equivalents, as will be appreciated by those of skill in the art with respect to the reporter moiety, the position of the linker, the type of linker and the associated substituents on the dinucleotide caps. ARCAs are as indicated.

Example 9

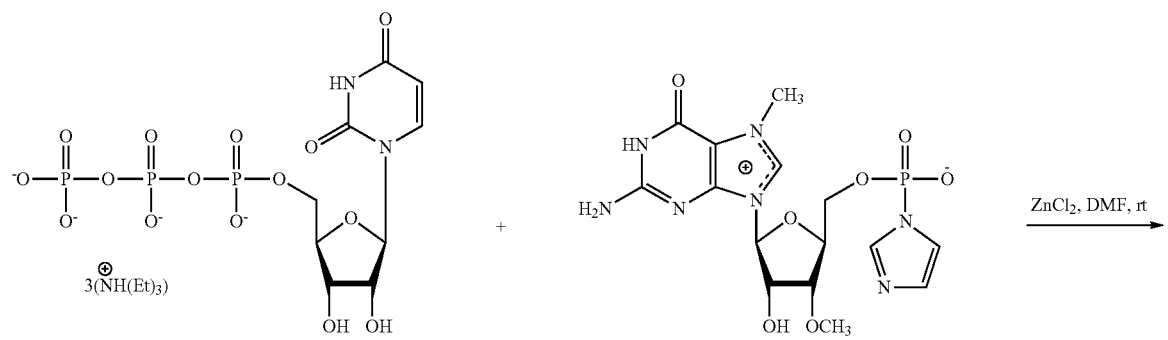

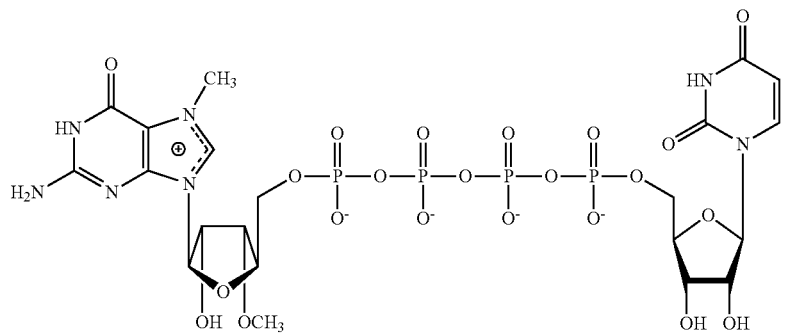

Synthesis of $m_2^{7,3'O}G[5']pppp[5']U$ (30)

To a stirred solution of UTP TEA salt (0.125 g, 0.17 mmol) and $m_2^{7,3'O}$ImGMP (0.075 g, 0.17 mmol), the synthesis of which is shown in Example 12, in 5.0 mL dry DMF, zinc chloride (0.046 g, 0.34 mmol) was added under nitrogen atmosphere and the reaction mixture was stirred at room temperature for 14 hr. After 14 hr, the reaction mixture was added to a solution of EDTA disodium (0.26 g, 0.68 mmol) in 100.0 mL of water at 0° C. The resulting aqueous solution was adjusted to pH 5.5 and loaded on a DEAE Sephadex column. The desired product was eluted using a linear gradient of 0-1M TEAB and the fractions containing the product were pooled, evaporated and concentrated to 10.0 mL TEA salt of $m_2^{7,3'O}G[5']pppp[5']U$ (30). The resulting 10.0 mL was passed through a Strata-X-AW column and washed with 10.0 mL water followed by 10.0 mL MeOH. Then, the desired compound was eluted with 15.0 mL of $NH_4OH/MeOH/H_2O$ (Feb. 25, 1973) and the collected solution was evaporated and dried to give a fine white powder (compound 30). (Yield: 0.078 g, 54%). The use of $m_2^{7,3'O}G[5']pppp[5']U$ as a control for comparison of yield of in vitro transcription and translation activity in order to compare results with novel mCAPs and ARCA caps conceived herewith.

Data for Compound 30: $^1$H NMR ($D_2O$, 400 MHz) δ 7.94 (d, J=8.0 Hz, 1H), 6.04 (d, J=4.4 Hz, 1H), 5.95 (m, 2H), 4.51 (m, 1H), 4.43-4.35 (m, 3H), 4.29-4.19 (m, 6H), 4.14 (s, 3H), 3.52 (s, 3H); $^{31}$P NMR ($D_2O$, 162 MHz) δ −10.27 (d, J=16.0 Hz) −21.92 (m); MS (m/z): 858 [M]$^+$. Used as a control for comparison of yield of in vitro transcription and translation activity.

Example 10

Synthesis of Compounds 1, 2, and 8

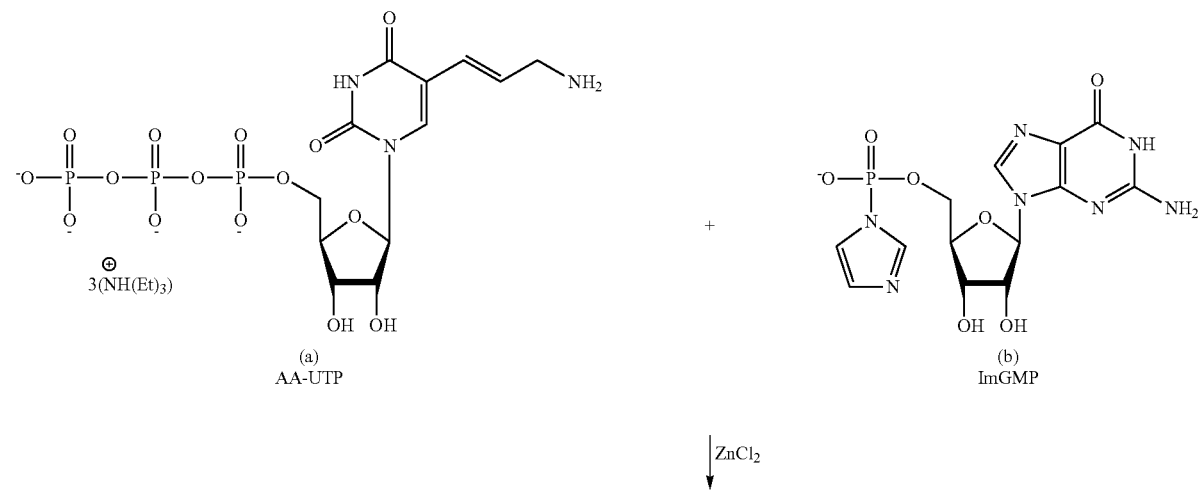

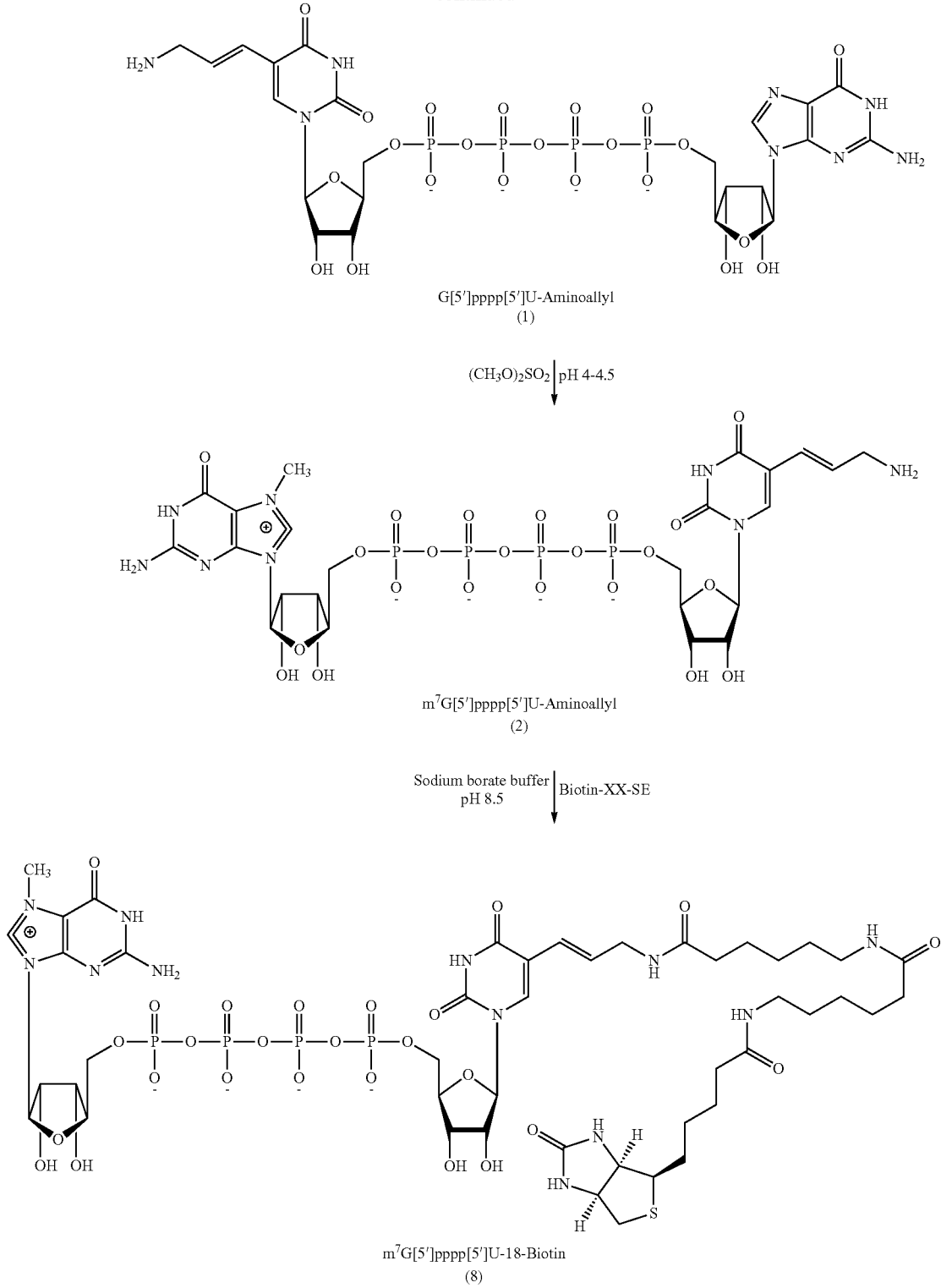

m<sup>7</sup>G[5′]pppp[5′]U-18-Biotin
(8)

Synthesis of G[5′]pppp[5′]U-Aminoallyl (1)

To an anhydrous solution of Imidazolyl GMP (400 mg, 0.78 mmol) and AA-UTP TEA (360.66 mg, 0.389 mmol) was added 4 equivalents of anhydrous $ZnCl_2$ (212.39 mg, 1.56 mmol) and the reaction mixture was stirred overnight. Then, the reaction mixture was stirred with 589.3 mg of EDTA in 25 mL of water for 10 min and the pH of the solution was adjusted with conc. $NaHCO_3$ to pH 5.5. The resultant solution was loaded onto a DEAE Sepharose column and eluted with 25-100% triethylammonium bicarbonate buffer (pH 7.5, 4° C.) to obtain pure G[5′]pppp[5′]U-Aminoallyl (1) (450 mg, 90.89%). The identity of compound (1) was confirmed by LC-MS and NMR spectrum. The molecular weight of this compound as revealed by MALDI-TOF is 885.33 Da (Expected Exact Mass is 884.03 Da).

Data for Compound (1): $^1$H NMR (D$_2$O, 400 MHz) δ 8.09 (s, 1H), 8.02 (s, 1H), 6.49 (d, J=16.4 Hz, 1H), 6.37 (m, 1H), 5.91 (d, J=4.0 Hz, 1H), 5.87 (d, J=6.0 Hz, 1H), 4.72 (t, J=6.0 Hz, 1H), 4.53 (m, 1H), 4.41-4.22 (m, 8H), 3.71 (d, J=6.4 Hz, 2H); $^{31}$P NMR (D$_2$O, 162 MHz) δ −9.95 (d, J=16.7 Hz, 1P), −10.12 (d, J=16.7 Hz, 1P), −21.40 (m, 2P); MS (m/z): 884 [M+H]$^+$.

Synthesis of m$^7$G[5']pppp[5']U-Aminoallyl (2)

To a stirred solution of 300 mg (0.236 mmol) of G[5']pppp[5']U-Aminoallyl (1) was slowly added 2.24 mL (23.6 mmol) of dimethyl sulfate. During the addition of dimethyl sulfate, the pH of the solution was maintained ~4.0 using a solution of concentrated NaOH. The progress of the reaction was monitored by analytical anion exchange HPLC. After the complete disappearance of starting material, the sample was loaded onto a DEAE Sepharose column and eluted with 25-100% triethylammonium bicarbonate buffer (pH 7.5, 4° C.) to obtain m$^7$G[5']pppp[5']U-Aminoallyl (2) in 82.36% yield (250 mg). The identity of this compound was confirmed by LC-MS and NMR spectrum. The molecular weight of this compound as revealed by MALDI-TOF is 899.69 Da (Expected Exact Mass is 899.05 Da).

Data for Compound (2): $^1$H NMR (D$_2$O, 400 MHz) δ 8.12 (s, 1H), 6.53 (d, J=16.4 Hz, 1H), 6.44 (m, 1H), 6.00 (d, J=3.6 Hz, 1H), 5.92 (d, J=4.0 Hz, 1H), 4.61 (m, 1H), 4.51 (d, J=5.2 Hz, 1H), 4.42-4.24 (m, 8H), 4.12 (s, 3H), 3.73 (d, J=6.0 Hz, 2H); $^{31}$P NMR (D$_2$O, 162 MHz) δ −10.27 (m, 2P), −21.73 (m, 2P); MS (m/z): 899 [M]$^+$.

Synthesis of m$^7$G[5']pppp[5']U-18-Biotin (8)

150 mg (0.152 mmol) of m$^7$G[5']pppp[5']U-Aminoallyl (2) was dissolved in 5 mL of 0.1 M sodium borate buffer (pH 8.5) and the solution was stirred for 15 min at room temperature. Immediately before use, a solution of 152.62 mg (0.228 mmol) of Biotin XX NHS ester in 2 mL of DMSO was prepared. To a stirred solution of m$^7$G[5']pppp[5']U-AA was added Biotin XX NHS ester slowly during a period of 10 min. The reaction was allowed to take place for 4 hr at room temperature. After 4 hr, the reaction mixture was loaded onto an AMBERCHROM™ XT20 RP column and eluted with 2-50% acetonitrile to obtain pure m$^7$G[5']pppp[5']U-18-Biotin (8) in 90.51% yield (198 mg). The molecular weight of this compound as revealed by MALDI-TOF is 1351.37 Da (Expected Exact Mass 1351.30 Da).

Data for compound (8): $^1$H NMR (D$_2$O, 400 MHz) δ 7.92 (s, 1H), 6.46 (m, 1H), 6.30 (d, J=16.0 Hz, 1H), 6.01 (d, J=4.0 Hz, 1H), 5.95 (d, J=6.0 Hz, 1H), 4.68-4.24 (m, 12H), 4.12 (s, 3H), 3.90 (m, 2H), 3.30 (m, 1H), 3.17 (t, J=6.8 Hz, 4H), 2.98 (dd, J=13.0, 5.0 Hz, 1H), 2.77 (d, J=13.2 Hz, 1H), 2.31 (t, J=6.8 Hz, 2H), 2.22 (m, 4H), 1.76-1.27 (m, 18H); $^{31}$P NMR (D$_2$O, 162 MHz) δ −10.29 (d, J=17.8 Hz, 1P), −10.66 (d, J=17.0 Hz, 1P), −22.08 (m, 2P); MS (m/z): 1351 [M]$^+$.

Compounds 1, 2 and 8 are also shown in FIG. 3 which illustrates the methylation of the N7 position of the guanosine by taking compound (1) and reacting it with dimethyl sulfoxide at a pH of 4.0-4.5 to provide compound (2), and the subsequent treatment of compound (2) with sodium borate buffer at pH 8.5 and Biotin-XX-SE to provide a reporter moiety tagged dinucleotide cap as illustrated by compound (8).

Example 11

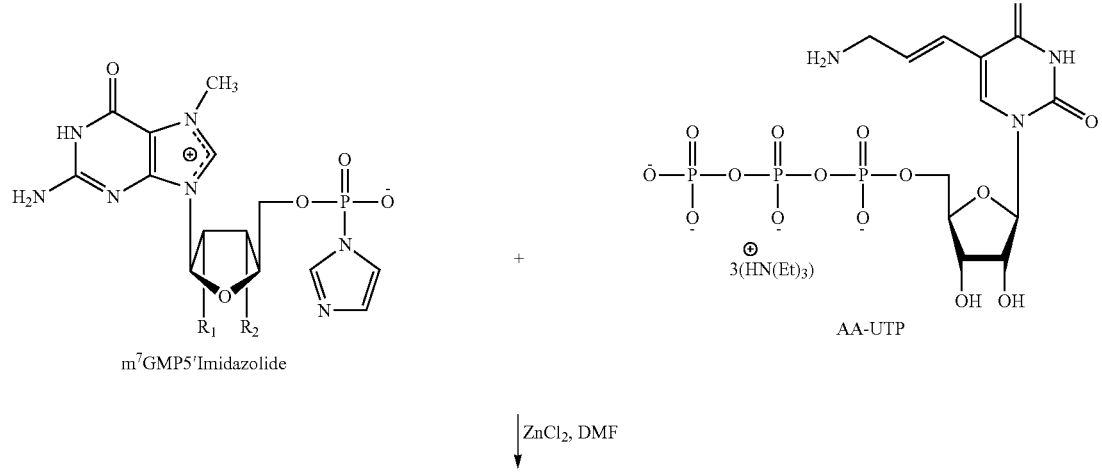

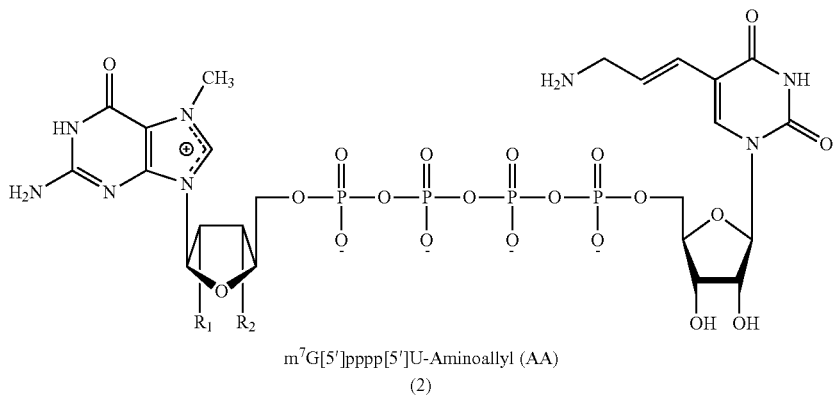

m⁷G[5']pppp[5']U-Aminoallyl (AA)
(2)

2: R₁ = OH, R₂ = OH    5: R₁ = F, R₂ = OH
3: R₁ = OH, R₂ = OCH₃  6: R₁ = OH, R₂ = H
4: R₁ = OCH₃, R₂ = OH

Scheme to Make Compounds 4, 5, and 6

The coupling reaction of Aminoallyl UTP with m₂$^{7,2'O}$ImGMP or m$^{7,2'F}$ImGMP or m⁷3'dImGMP in the presence of ZnCl₂ provides the corresponding compounds 4, 5, and 6, respectively.

Example 12

Preparation of m₂$^{7,3'O}$G[5']pppp[5']U-Aminoallyl (3)

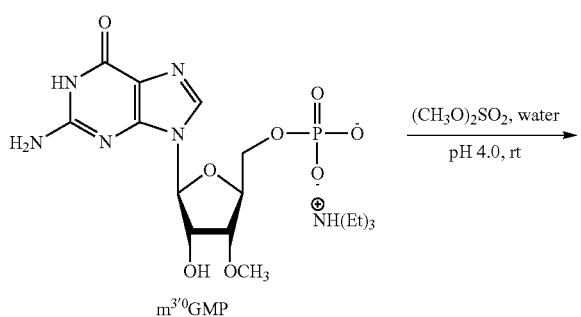

m³'ᵒGMP

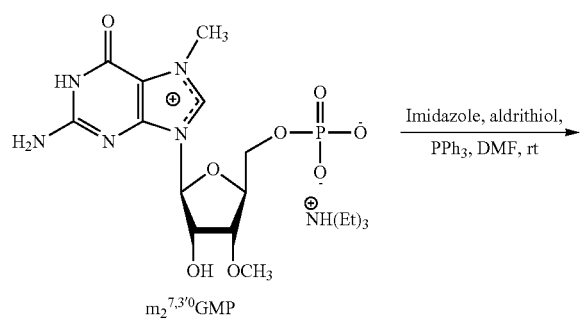

m₂$^{7,3'0}$GMP

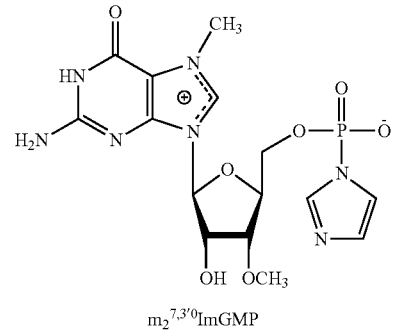

m₂$^{7,3'0}$ImGMP (a) Preparation of m₂$^{7,3'O}$ImGMP:
(i) Preparation of m₂$^{7,3'O}$GMP:

To a stirred solution of m³'ᵒGMP (1.50 g, 3.14 mmol) in 50.0 mL of water, acetic acid was added slowly to adjust the pH of the solution to 4.0. To this mixture, dimethyl sulfate (3.0 mL) was added drop wise over a period of 30 min and the reaction mixture was allowed to stir at room temperature for 3 hr. As the methylation proceeds, the pH drops down to around 2.0 and was readjust back to pH 4.0 using 1M NaOH solution. After 3 hr, the reaction mixture was extracted with CHCl₃ (3×50) to remove unreacted excess dimethyl sulfate. The collected aqueous solution was adjusted to pH 5.5 with glacial acetic acid and loaded on a DEAE Sephadex column. The desired product was eluted using a linear gradient of 0-1M TEAB, pH 7.5 and the fractions containing the product were pooled, evaporated and dried in vacuum desiccator over phosphorous pentoxide to give a fine white powder of m₂$^{7,3'O}$GMP along with excess triethylammonium bicarbonate salt (Yield 11.2 g).

(ii) Synthesis of m₂$^{7,3'O}$ImGMP:

To a stirred solution of m₂$^{7,3'O}$GMP (11.2 g) in 50 mL dry DMF, imidazole (1.07 g, 15.7 mmol), triphenylphosphine (1.64 g, 6.28 mmol), aldrithiol (1.38 g, 6.28 mmol) and triethylamine (0.32 g, 3.14 mmol) were added. The reaction mixture was stirred under nitrogen atmosphere at room temperature overnight. Then, the reaction mixture was filtered to obtain a clear filtrate. To a solution of sodium perchlorate (2.0 g) in 100 mL acetone in a centrifuge tube at 0° C., the above clear filtrate was added slowly for 5 minutes. The resulting mixture was centrifuged and the supernatant liquid was removed. The solid was ground with a new portion of acetone (100 mL), cooled, and centrifuged again. This process was repeated twice and the resulting solid was dried in a vacuum desiccator over $P_2O_5$ to give a white powder, $m_2^{7,3'O}$ImGMP (Yield: 0.62 g, 45%—Isolated overall yield based on the starting $m_2^{7,3'O}$GMP)

(b) Conjugation of AA-UTP with $m_2^{7,3'O}$ImGMP:

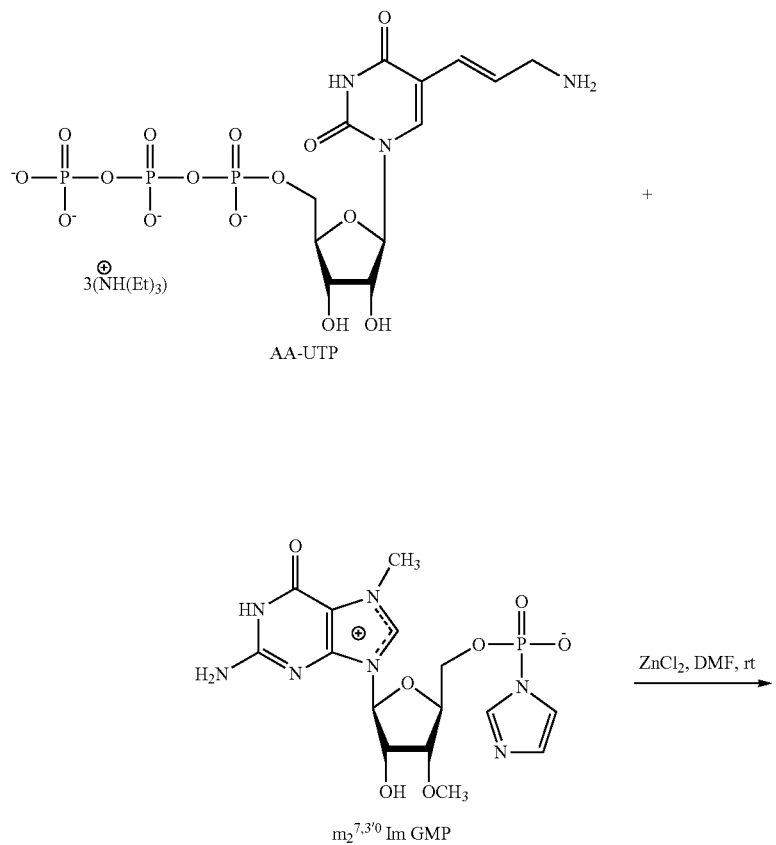

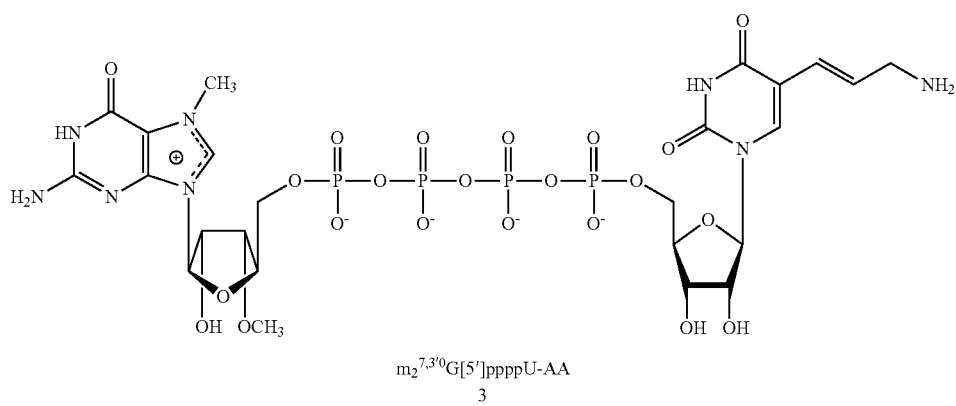

The coupling reaction of AA-UTP with $m_2^{7,3'O}$ImGMP in the presence of $ZnCl_2$ provides the corresponding $m_2^{7,3'O}$G[5']pppp[5']U-Aminoallyl (3).

Example 13

Scheme to Make G[5']pppp[5']U-18-Biotin and G[5']pppp[5']C-18-Biotin

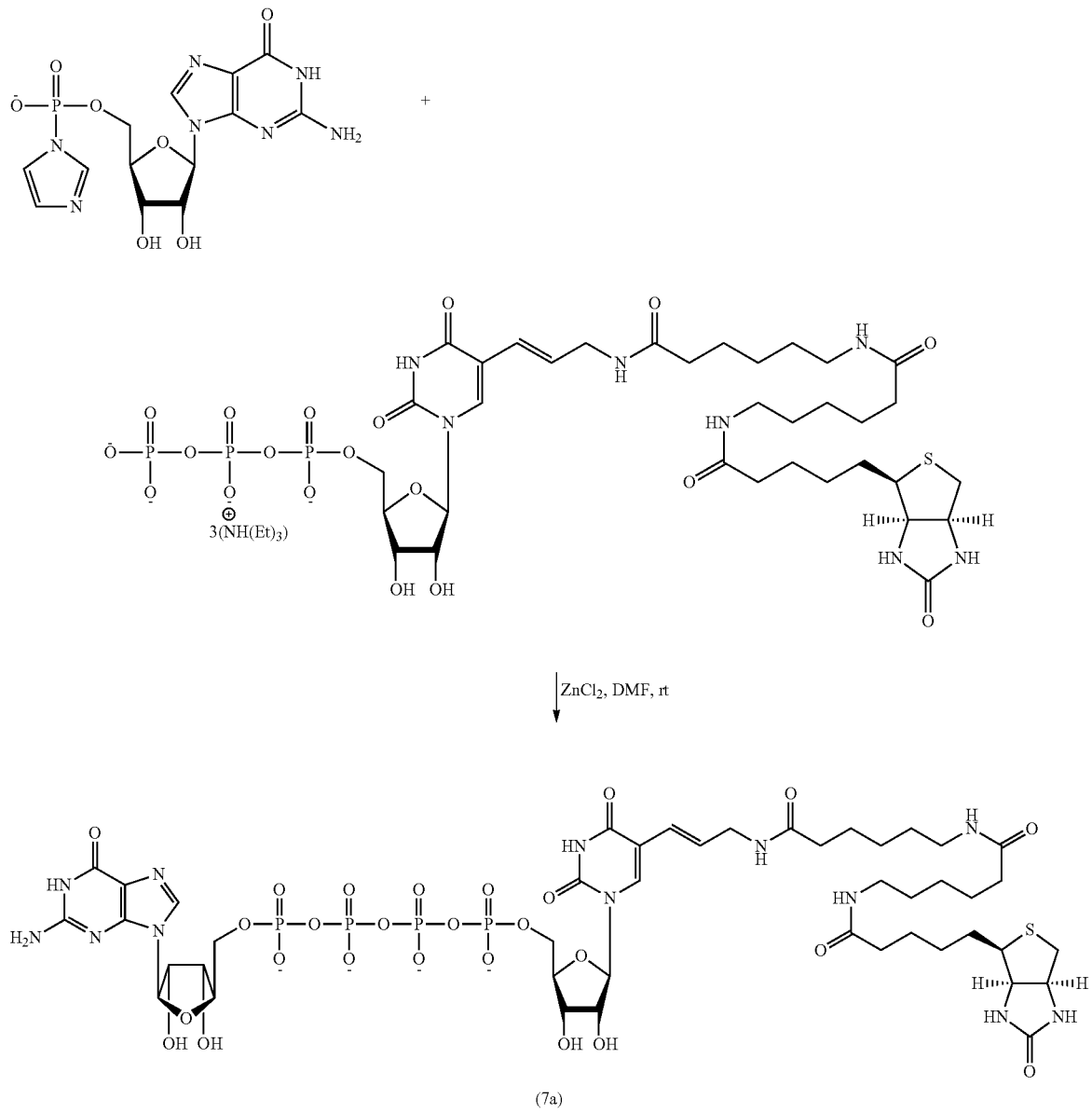

(7a)

Synthesis of GppppU-18-Biotin (7a)

To an anhydrous solution of Imidazolyl GMP (100 mg, 0.195 mmol) and Bio-18-UTP TEA (223.73 mg, 0.162 mmol) was added 4 equivalents of anhydrous $ZnCl_2$ (88.49 mg, 0.65 mmol) and the reaction mixture was stirred overnight. The reaction mixture was stirred with 188 mg of EDTA for 10 min and the pH of the solution was adjusted with conc. $NaHCO_3$ to 5.5. The resultant solution was loaded onto a DEAE Sepharose column and eluted with 25-100% triethylammonium bicarbonate buffer (pH 7.5, 4° C.) to obtain pure GppppU-18-Bio (7) (230 mg, 82.21%). The identity of compound 3 was confirmed by LC-MS and NMR spectrum.

Data for compound (7a): $^1$H NMR ($D_2O$, 400 MHz) δ 8.12 (s, 1H), 7.88 (s, 1H), 6.41 (m, 1H), 6.23 (d, J=16.0 Hz, 1H), 5.96 (d, J=5.6 Hz, 1H), 5.87 (d, J=6.4 Hz, 1H), 4.58 (m, 2H), 4.46-4.26 (m, 10H), 3.88 (m, 2H), 3.28 (m, 1H), 3.15 (m, 4H), 2.97 (dd, J=13.0, 5.0 Hz, 1H), 2.76 (d, J=13.2 Hz, 1H), 2.32-2.19 (m, 6H), 1.73-1.24 (m, 18H); $^{31}$P NMR ($D_2O$, 162 MHz) δ −10.25 (d, J=20.4 Hz, 1P), −10.57 (d, J=20.5 Hz, 1P), −22.09 (m, 2P); MS (m/z): 1337 [M+H]$^+$.

Synthesis of G[5']pppp[5']C-18-Biotin (7b)

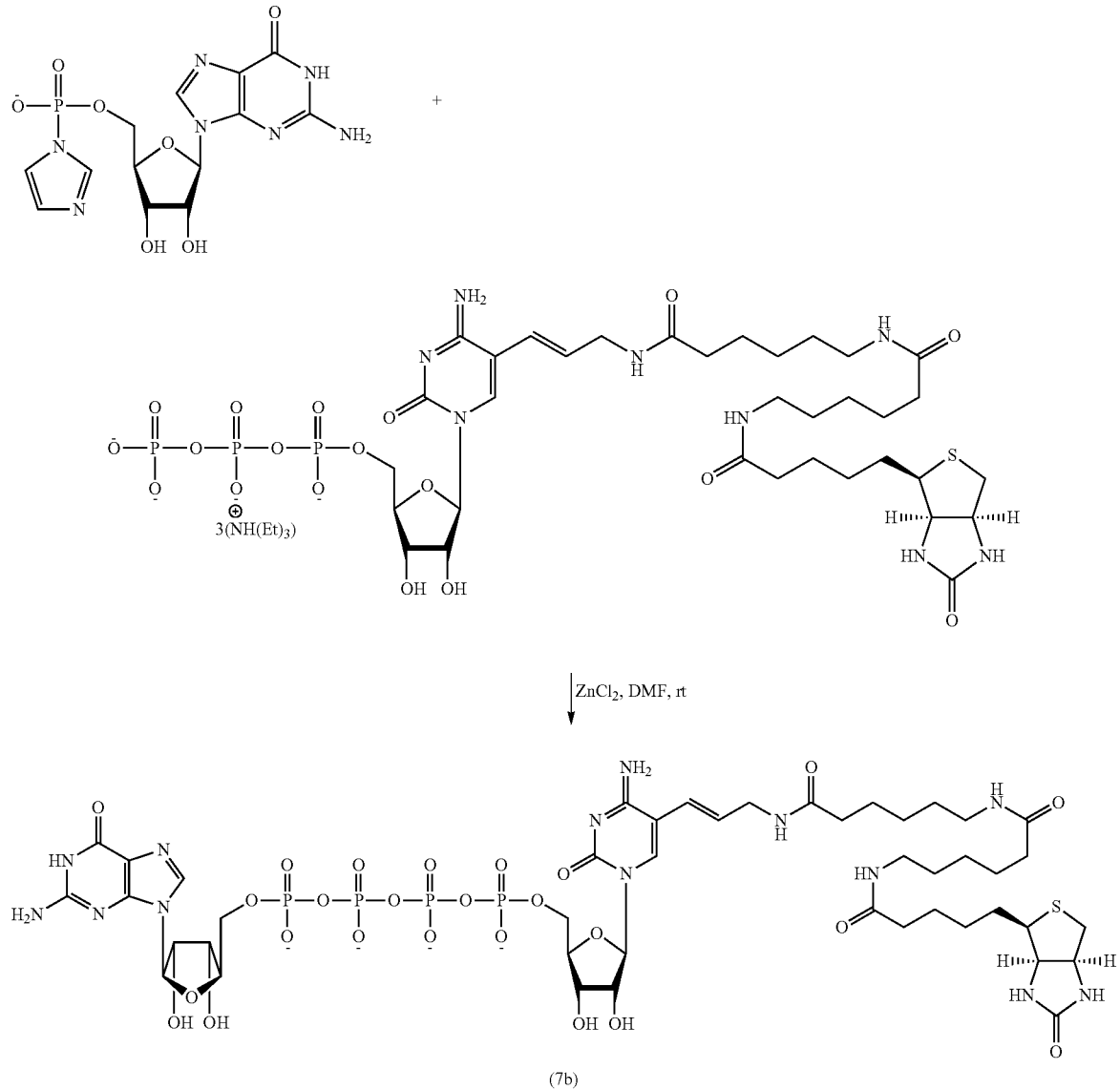

(7b)

The coupling reaction of ImGMP with Bio-18-CTP TEA salt in the presence of ZnCl2 provides the corresponding G[5']pppp[5']C-18-Biotin (7b).

Compound 7a is also shown in FIG. 2, as the attached biotin-linker-nucleobase disclosed in the structure labeled Bio-18UTP. Each of the structures shown in FIG. 2 are examples of a non-cleavable linker attached to a dinucleotide cap of the present invention.

Example 14

Synthesis of $m_2^{7,3'O}$G[5']pppp[5']U-Aminoallyl-18-Biotin (9)

To a stirred solution of aminoallyl UTP (0.08 g, 0.085 mmol) and $m_2^{7,3'O}$ImGMP (0.075 g, 0.17 mmol) in 5.0 mL dry DMF, $ZnCl_2$ (0.023 g, 0.17 mmol) was added under nitrogen atmosphere and the reaction mixture was stirred at room temperature for 6 hr. After 6 hr, the reaction mixture was added to a solution of EDTA disodium (0.13 g, 0.34 mmol) in 100.0 mL of water at 0° C. The resulting aqueous solution was adjusted to pH 5.5 with glacial acetic acid and loaded on a DEAE Sephadex column. The desired product was eluted using a linear gradient of 0-1M TEAB, pH 7.5 and the fractions containing the product were pooled, evaporated and concentrated to 10.0 mL TEA salt of (9). The resulting 10.0 mL was passed through a Strata-X-AW column and washed with 10.0 mL water followed by 10.0 mL MeOH. Then, the desired compound was eluted with 15.0 mL of $NH_4OH$/MeOH/$H_2O$ (Feb. 25, 1973) and the collected solution was evaporated and dried to give a fine white powder (9). (Yield: 0.034 g, 41%).

Data for Compound (9): $^1$H NMR ($D_2O$, 400 MHz) δ 8.10 (s, 1H), 6.52 (d, J=16.0 Hz, 1H), 6.43 (m, 1H), 5.98 (d, J=3.6.0 Hz, 1H), 5.91 (d, J=6.0 Hz, 1H), 4.46-4.15 (m, 12H), 4.12 (s, 3H), 3.72 (d, J=5.6 Hz, 2H), 3.49 (s, 3H); $^{31}$P NMR ($D_2O$, 162 MHz) δ −10.27 (m, 2P), −21.79 (m, 2P); MS (m/z): 911 [M+2H]$^+$.

Example 15

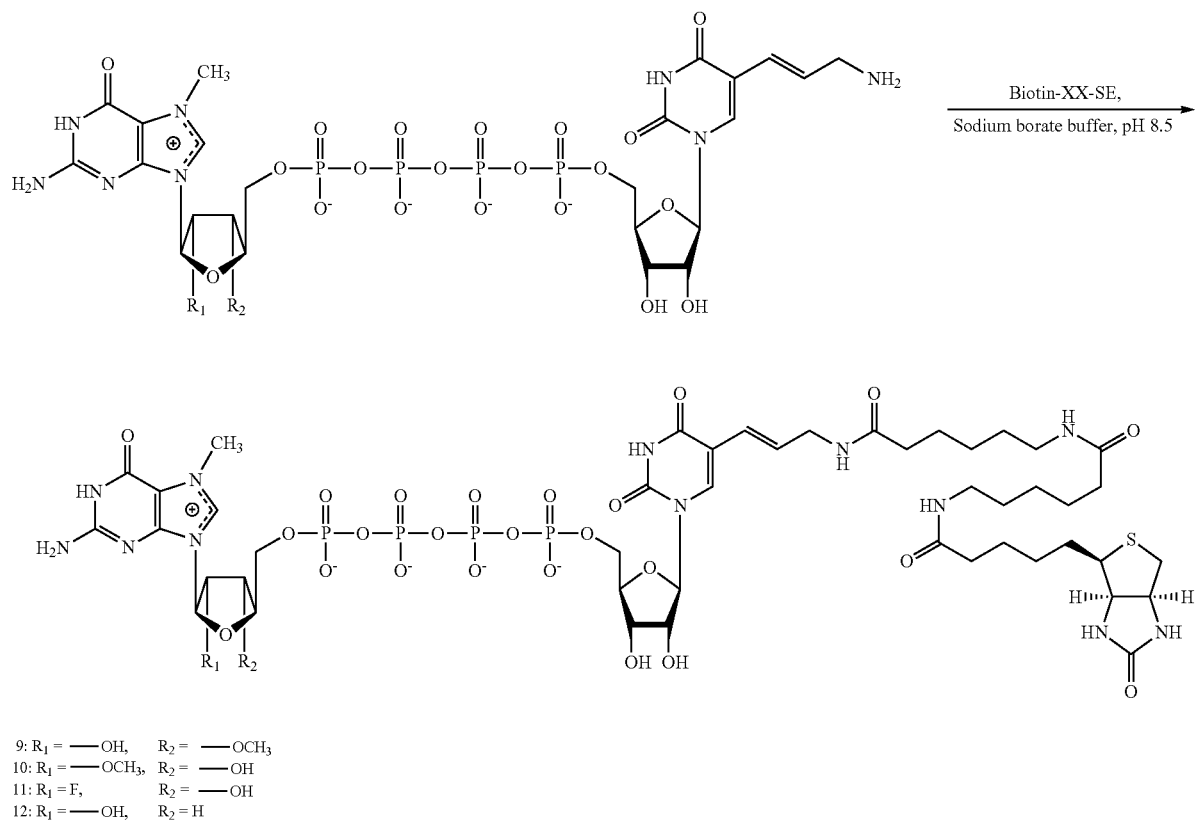

9: $R_1 = $ —OH,  $R_2 = $ —OCH$_3$
10: $R_1 = $ —OCH$_3$, $R_2 = $ —OH
11: $R_1 = $ F, $R_2 = $ —OH
12: $R_1 = $ —OH, $R_2 = $ H

Scheme to Make Compounds 10, 11, and 12

The coupling reaction of m$_2^{7,2'O}$G[5']pppp[5']U-Aminoallyl, m$^{7,2'F}$G[5']pppp[5']U-Aminoallyl, or m$^7$3' dG[5']pppp[5']U-Aminoallyl with Biotin-XX-SE in the presence of sodium borate buffer affords the corresponding compounds 10, 11, and 12, respectively.

Compounds 9-12 as illustrated have a non-cleavable linker. The structure illustrated in FIG. 1 can correspond to compounds 9 and 12 having four phosphate molecules connecting the nucleobases of the dinucleotide cap with a cleavable linker as indicated by the presence of the disulfide (S—S) bond within the carbon chain of the biotin reporter moiety. An alternative synthesis scheme for compounds 9 and 12 is also shown in FIG. 4.

Example 16

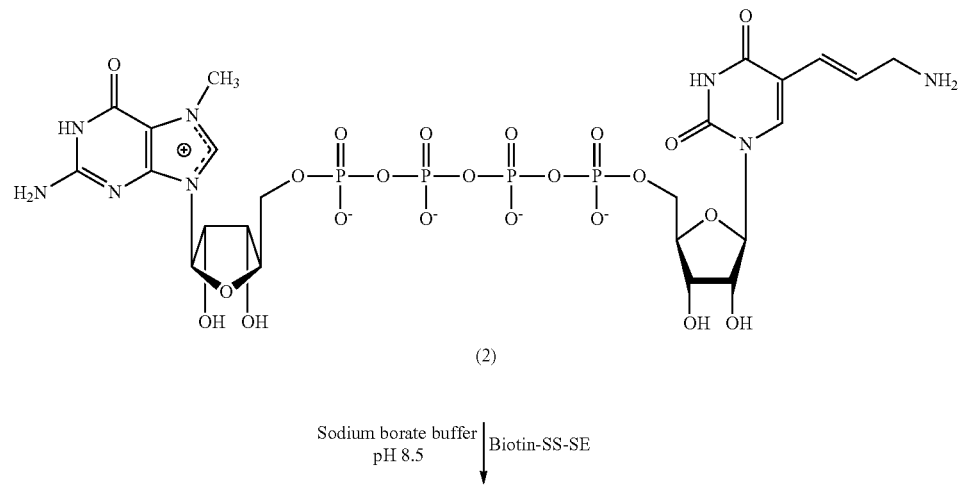

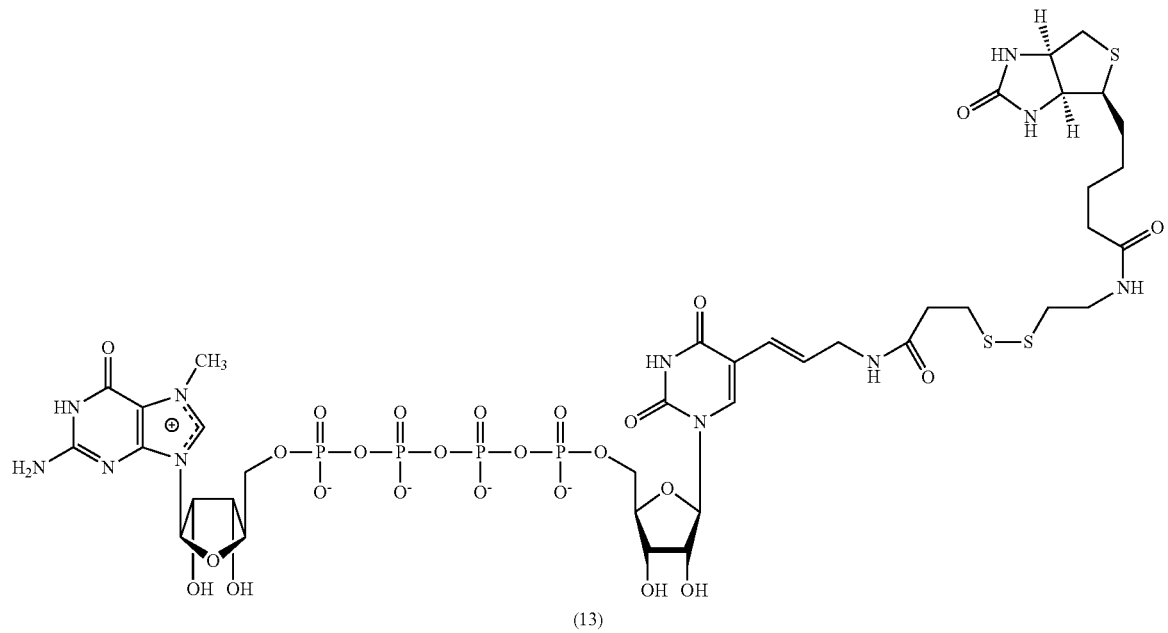

(13)

Synthesis of m⁷G[5']pppp[5']U—SS-Biotin (13)

60 mg (0.067 mmol) of m⁷G[5']pppp[5']U-Aminoallyl (2) was dissolved in 5 mL of 0.1 M sodium borate buffer (pH 8.5) and the solution was stirred for 15 min at room temperature. Immediately before use, a solution of 50.72 mg (0.101 mmol) of Biotin-SS—SE NHS ester in 2 mL of DMSO was prepared. To a stirred solution of m⁷G[5']pppp[5']U-AA was added Biotin-SS—SE NHS ester slowly during a period of 10 min. The reaction was allowed to take place for 4 hr at room temperature. After 4 hr, the reaction mixture was loaded onto an AMBERCHROM™ XT20 RP column and eluted with 2-50% acetonitrile to obtain pure m⁷G[5']pppp[5']U—SS-Biotin (13) in 83.62% yield (72 mg). The molecular weight of this compound as revealed by MALDI-TOF was 1351.37 Da (Expected Exact Mass 1351.30 Da).

Compound 13 is depicted as having a cleavable linker as indicated by the presence of a disulfide (S—S) bond in the carbon chain of the biotin molecule. This compound is also depicted in FIG. 1 and in FIG. 4 which illustrates a scheme for the synthesis of compounds 12, 13, and 14.

Example 17

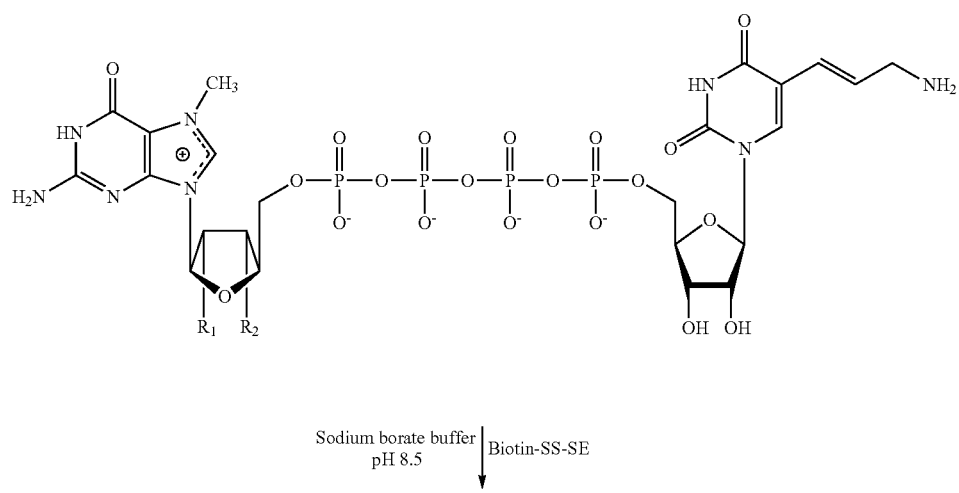

-continued

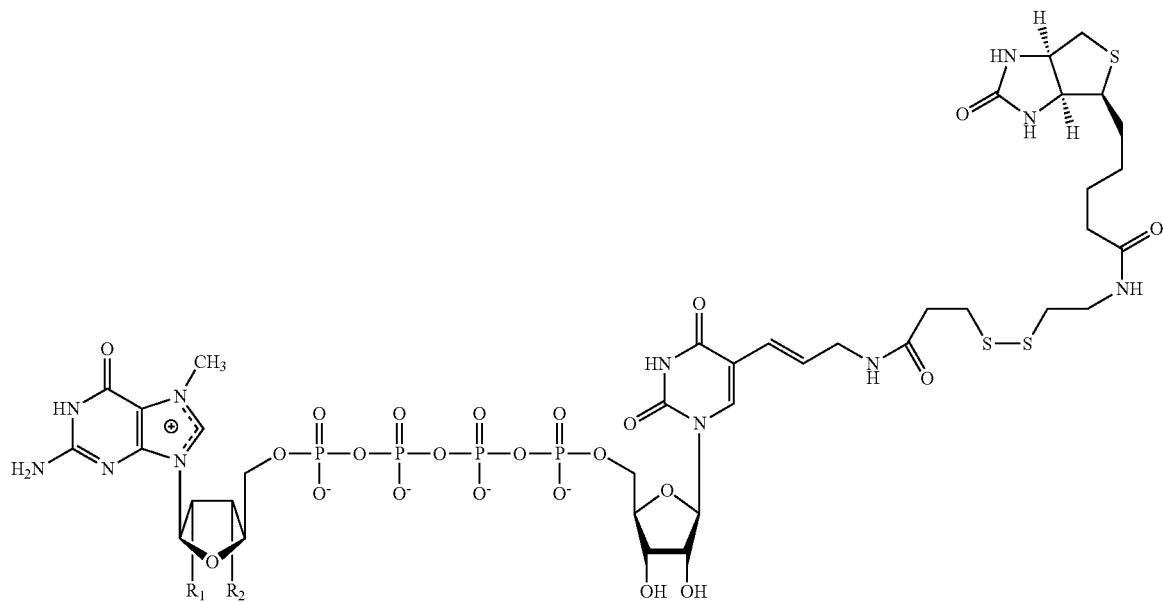

14: $R_1 =$ —OH, $R_2 =$ —OCH$_3$
15: $R_1 =$ —OCH$_3$, $R_2 =$ —OH
16: $R_1 =$ —F, $R_2 =$ —OH
17: $R_1 =$ —OH, $R_2 =$ H

Scheme to Make Compounds 14, 15, 16, and 17

The coupling reaction of m$_2^{7,3'O}$G[5']pppp[5']U-Aminoallyl or m$_2^{7,2'O}$G[5']pppp[5']U-Aminoallyl or m$^{7,2'F}$G[5']pppp[5']U-Aminoallyl or m$_2^{7}$3'dG[5']pppp[5']U-Aminoallyl with Biotin-SS—SE in the presence of sodium borate buffer affords the corresponding compounds 14, 15, 16, and 17, respectively.

Compounds 14 and 17 are depicted as having a cleavable linker as indicated by the presence of a disulfide (S—S) bond in the carbon chain of the biotin molecule. These compound are also depicted in FIG. 1 and in FIG. 4 which illustrates a scheme for the synthesis of compounds 14 and 17.

Example 18

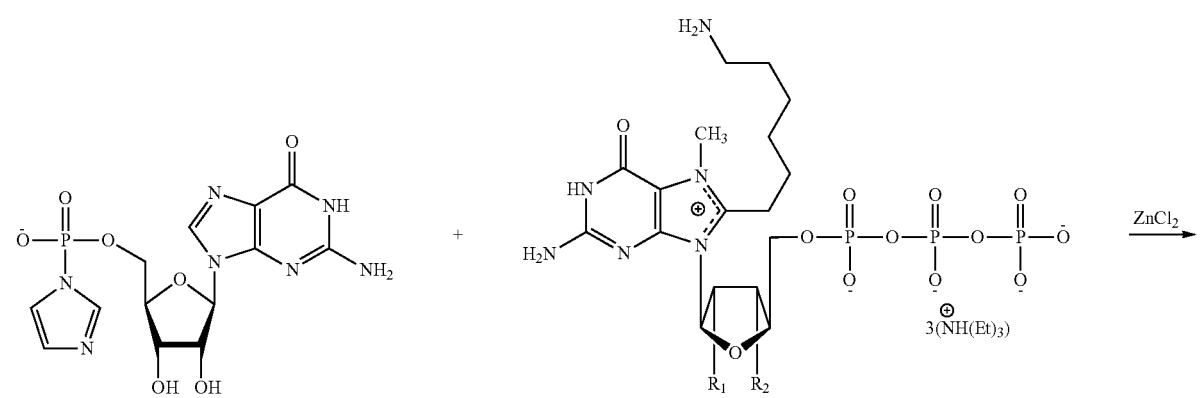

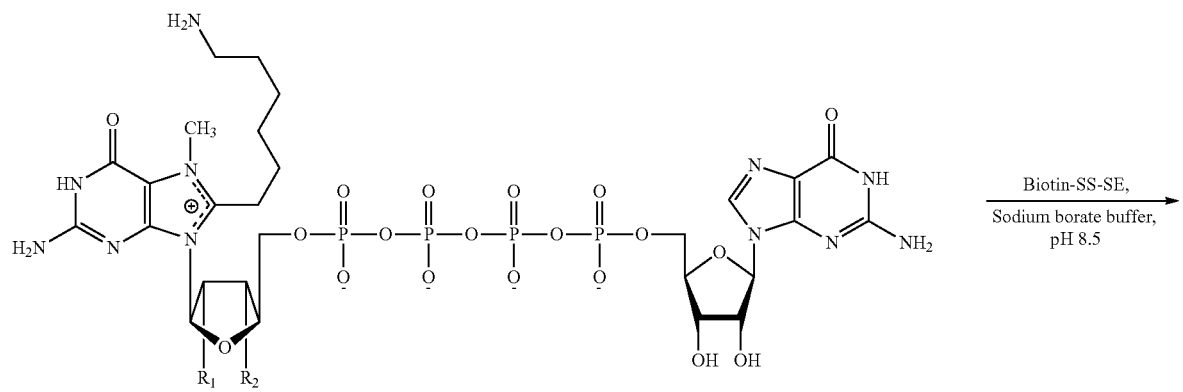

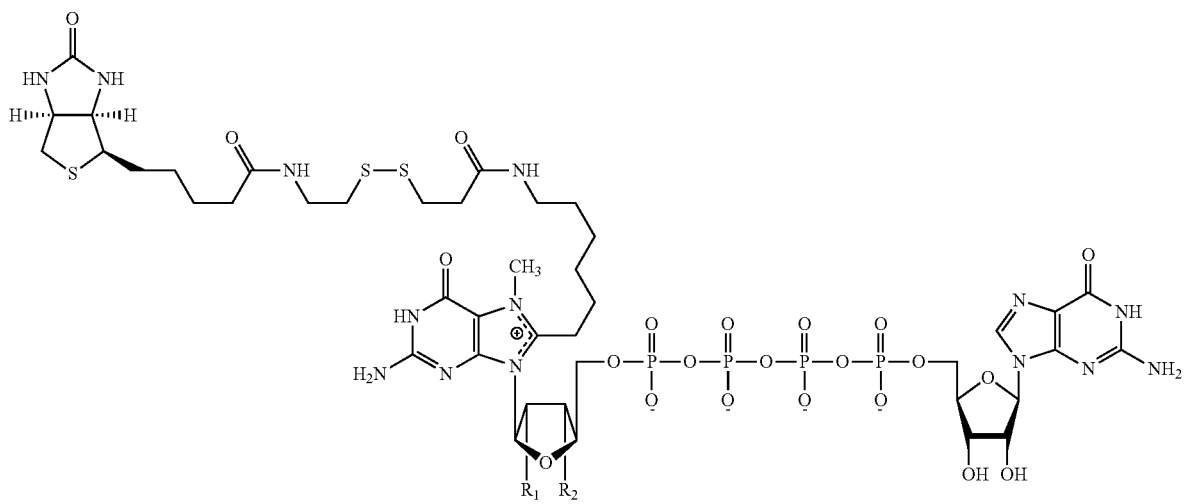

18: $R_1 =$ —OH, $R_2 =$ —OH
19: $R_1 =$ —OH, $R_2 =$ —OCH$_3$
10: $R_1 =$ —OCH$_3$, $R_2 =$ —OH
21: $R_1 =$ —F, $R_2 =$ —OH
22: $R_1 =$ —OH, $R_2 =$ —H

Scheme to Make Compounds 18-22

The coupling reaction of ImGMP with the modified C8-position ($R_5$) of m$^7$GDP or m$^7$GTP also containing 2' or 3' modifications provides the corresponding cleavable, biotinylated cap analog in the presence of ZnCl$_2$. Cap analog m$^{7,8\text{-}S\text{—}S\text{-}Biotin}$G[5']pppp[5']Nuc (18), Cap analog
m$_2^{7,3'O,8\text{-}S\text{—}S\text{-}Biotin}$G[5']pppp[5']Nuc (19), Cap analog
m$_2^{7,2'O,8\text{-}S\text{—}S\text{-}Biotin}$G[5']pppp[5']Nuc (20), Cap analog
m$_2^{7,2'F,8\text{-}S\text{—}S\text{-}Biotin}$G[5']pppp[5']Nuc (21), and Cap analog
m$^{7,8\text{-}S\text{—}S\text{-}Biotin}$3'dGG[5']pppp[5']Nuc (22).

Example 19

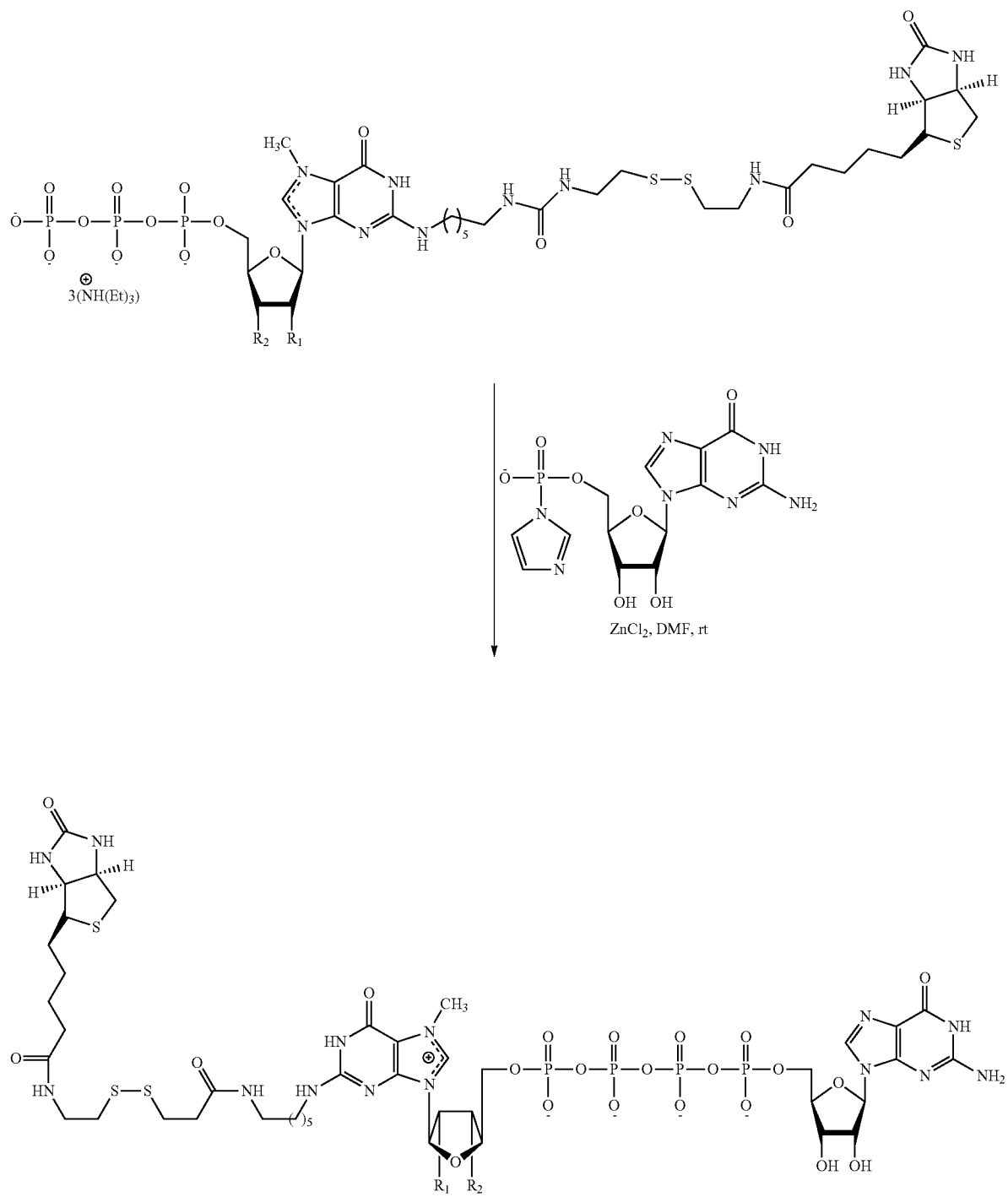

23: $R_1 =$ —OH, $R_2 =$ —OH
24: $R_1 =$ —OH, $R_2 =$ —OCH$_3$
25: $R_1 =$ —OCH$_3$, $R_2 =$ —OH
26: $R_1 =$ —F, $R_2 =$ —OH
27: $R_1 =$ —OH, $R_2 =$ —H

Scheme to Make Compounds 23-27

The coupling reaction of ImGMP with the corresponding substituted 2-S—S-BiotinGTP at the modified NH$_2$-position ($R_4$) of m$^7$GDP or m$^7$GTP also containing 2' or 3' modifications provides the corresponding cleavable, biotinylated cap analog in the presence of ZnCl$_2$ provides the corresponding compounds 23, 24, 25, 26 and 27, respectively.

Example 20
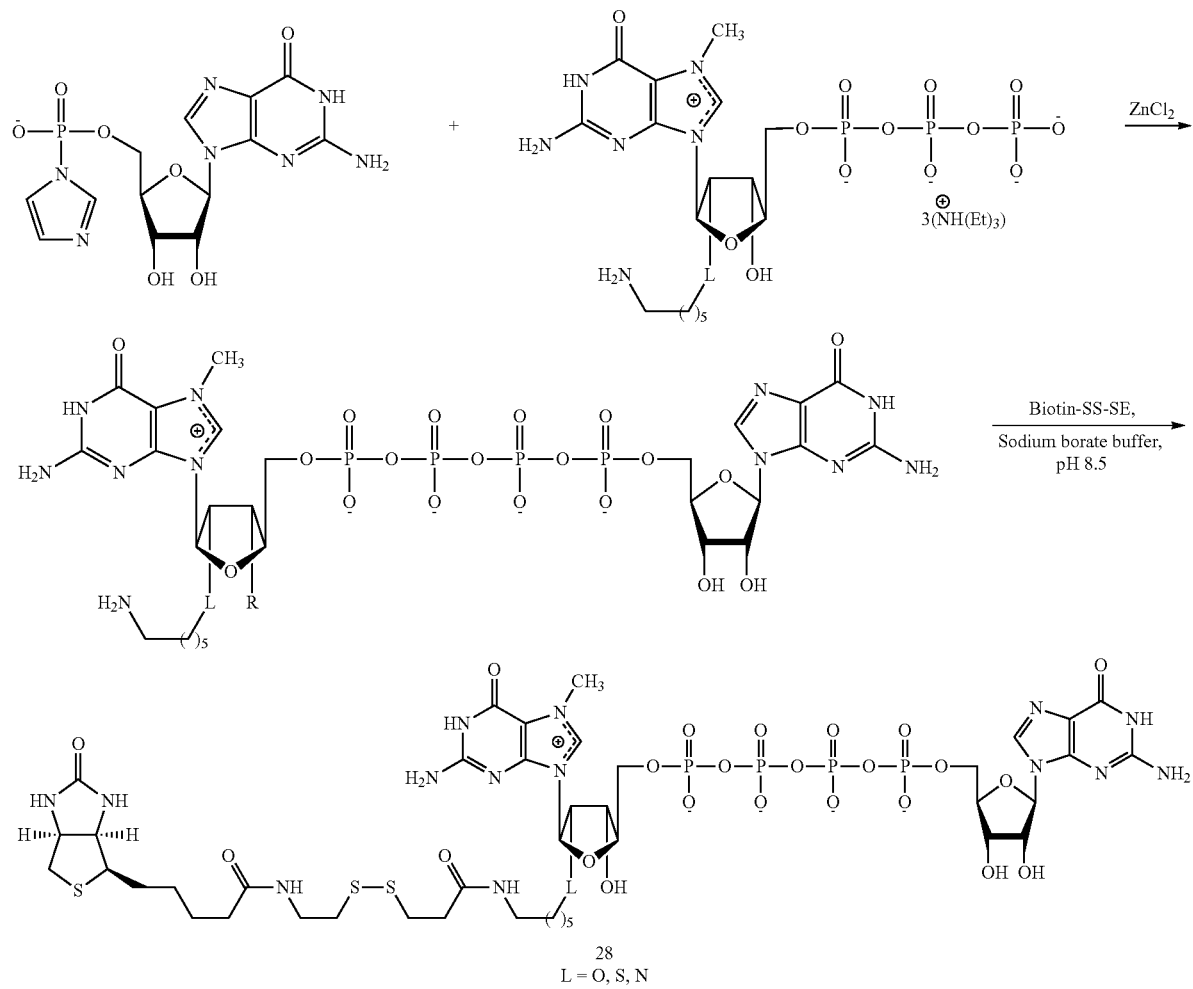
Scheme to Make m[7,2'-S—S-Biotin]G[5']pppp[5']Nuc, Compound 28
The coupling reaction of ImGMP with 2' modified m[7,2'-S—S-Bio]GTP in the presence of $ZnCl_2$ provides the corresponding cap analog compound 28.
Example 21
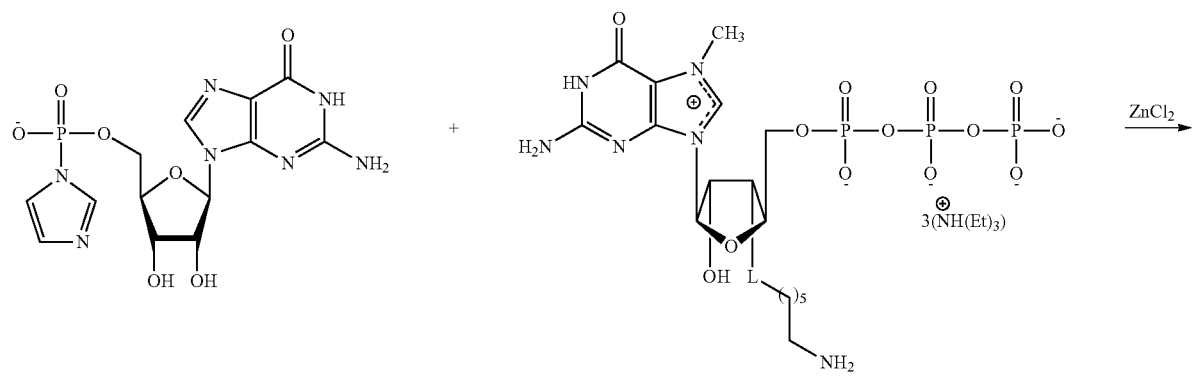

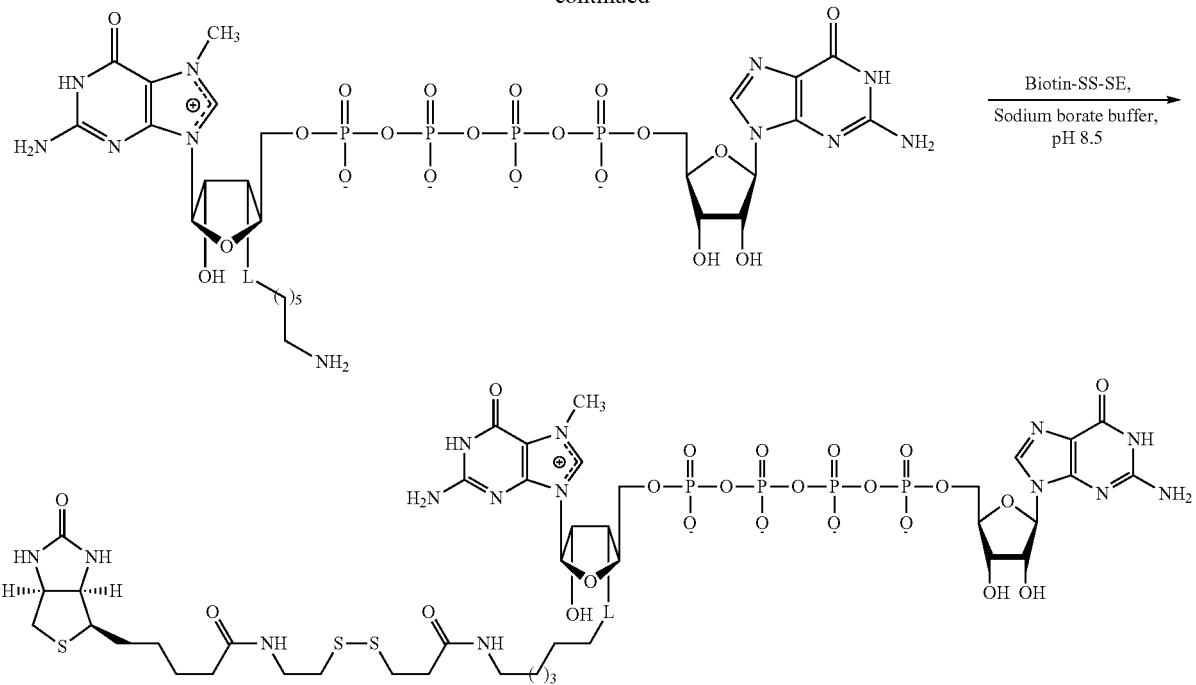

29
L = O, S, N

Scheme to Make m[7,3'-S—S-Biotin]G[5']pppp[5']Nuc, Compound 29

The coupling reaction of ImGMP with 3' modified m[7,3'-S—S-Bio]GTP in the presence of ZnCl$_2$ provides the corresponding cap analog compound 29.

Example 22

Synthesis of Biotin-18-UTP TEA (31)

1.444 g (2.06 mmol) of Allylamine UTP (AA-UTP) (a) was dissolved in 40 mL of 0.1 M sodium borate buffer (pH 8.5) and the solution was stirred for 15 min at room temperature. Immediately before use, a solution of 1.517 g (2.266 mmol) of Biotin XX-SE-NHS ester in 10 mL of DMSO was prepared. To a stirred solution of AA-UTP was added Biotin XX-SE-NHS ester slowly during a period of 20 min. The reaction was allowed to take place for 4 hr at room temperature. After 4 hr, the reaction mixture was loaded onto a DEAE Sepharose column and eluted with 1-100% triethylammonium bicarbonate buffer (pH 7.5, 4° C.) to obtain pure Bio-18-UTP TEA (31). The molecular weight of this compound as revealed by MALDI is 992.01 Da (Expected Exact Mass 992.26 Da). The structure of (31) is shown in FIG. 2.

Data for Compound 31: $^1$H NMR (D$_2$O, 400 MHz) δ 8.97 (s, 1H), 6.45 (m, 1H) 6.32 (d, J=16.4 Hz, 1H), 6.00 (d, J=5.2 Hz, 1H), 4.61 (m, 1H), 4.50-4.42 (m, 3H), 4.32-4.22 (m, 3H), 3.92 (m, 2H), 3.31 (m, 1H), 3.17 (t, J=6.8 Hz, 4H), 2.98 (dd, J=13.2, 5.2 Hz, 1H), 2.77 (d, J=12.8 Hz, 1H), 2.34-2.20 (m, 6H), 1.74-1.25 (m, 18H); $^{31}$P NMR (D$_2$O, 162 MHz) δ −7.27 (d, J=19.9 Hz, 1P), −10.39 (d, J=20.6 Hz, 1P), −21.23 (t, J=19.8 Hz, 1P); MS (m/z): 992 [M+11]$^+$.

Example 23

Scheme to Isolate Capped RNA

Cap analogs containing a reporter moiety allow for isolation and purification of only the capped RNA following transcription. Such isolation methods are readily known to one of skill in the art. FIG. 5-8 illustrate schemes for the isolation of purified capped mRNA having biotin as the reporter moiety. The capped mRNA is captured by using streptavidin-coated magnetic beads which act as a solid matrix and have a high affinity for biotin. Uncapped RNA will not be bound by the solid matrix and will be subsequently washed out. The bound, capped mRNA will be dissociated from the reporter moiety attached to the solid matrix by using either a 50 mM DTT or 100 mM β mercaptoethanol solution and then recovered and purified by using a spin column. The resulting capped RNA is ready for transfection and translation experiments and assays. This kind of technology is applicable for universal labeling and detaching, and has important applications in vaccine production as well as an important impact in the field of therapeutics.

Also envisioned is a kit containing a biotinylated cap analog. A user would synthesize an RNA transcript with at least one biotin reporter moiety or attach the biotin reporter moiety post-translation and subsequently isolate the capped RNA. The cap would be attached to the 5' end of the mRNA transcript. The kit would also comprise streptavidin-coated beads (possibly magnetic) and free biotin to elute the RNA from the streptavidin as shown in FIG. 5-8. The resulting isolated RNA could be used in experiments to identify proteins and RNA that bind to it. Protein analysis can be performed on a mass spectrometer instrument, as would be understood by the skilled artisan.

Once the 5' biotinylated-labeled RNA is isolated it can be used for pull down experiments to study RNA-protein interactions. First, the biotinylated RNA will be subjected to binding of protein. The binding between 5' biotinylated RNA and Rat Brain lysate (protein source) can be induced by incubation in a binding buffer (20 mmol Tris, 1 M NaCl, 1 mM EDTA, 0.02% Triton X-100, pH 8.0) for 10 mM with either unmodified non-full length (NFL) 3' UTR (−) or biotinylated cap NFL 3' UTR. After binding, the NFL 3' UTR ribonuclease phosphate (RNP) complexes were pulled down with Globin Clear Streptavidin beads (100 μL per sample). The pull down of the RNP complexes will be analyzed by Western blots. (A. Lal et al. *The EMBO Journal* 23, 3092-3102, (2004); R. Pullmann, Jr. et al. *The Journal of Biological Chemist*, 281 (33), 23456-23463, (2006)).

Example 24

Disulfide Bond Cleavage

The disulfide bond (S—S) can be cleaved under mild reducing conditions with agents such as 50 mmol dithiothreitol (DTT) or Tris(2-carboxyethyl)phosphine hydrochloride, (TCEP) or 100 mmol 2-Mercaptoethanol, and or 1% Sodium borohydride (Shimkus, M., et al. (1985). Proc. Natl. Acad. Sci. USA 82, 2593-2597; Dawson, B. A., et al. (1989). J. Biol. Chem. 264(22), 12830-12837; Kirkley, T. L., Anal. Biochem, 180, 231-236 (1989); Andrews, P. C., Dixon, J. E., Anal. Biochem, 161, 524-528 (1987); Schonberg, A., Chem. Ber., 163-164 (1935); Rauhut, M., et. al., JACS, 81, 1103-1107 (1959).

Schemes for the isolation of capped RNA and cleavage of the reporter moiety at the disulfide bond are illustrated in FIG. 5-8. The presence of the linker, aminoallyl, on the dinucleotide cap compound facilitates the attachment of the reporter moiety, biotin, as the example in FIG. 5-8, to the dinucleotide cap.

Example 25

T7 RNA Transcription

T7 RNA polymerase transcription was performed by using mMessage mMachine® T7 kit (Ambion) in 20 μL final volume, and contains the following reagents at the final concentrations indicated: 1 μg linearized AmbLuc PolyA DNA, 1× reaction buffer, 7.5 mmol of each ATP, UTP, and CTP, 1.5 mmol GTP, 6.5 mmol of mCAP and 2' fluoro cap analogs, and 50 U/μL of T7 RNA polymerase. The transcription reactions were incubated at 37° C. for 2 hours. In order to hydrolyze the remaining plasmid DNA, 1 μL of turbo DNAse was added to the reaction mixture, and further incubated at 37° C. for 15 minutes. The transcribed capped and uncapped mRNAs were purified by using the MEGAclear™ Kit (Ambion).

Figure 10:
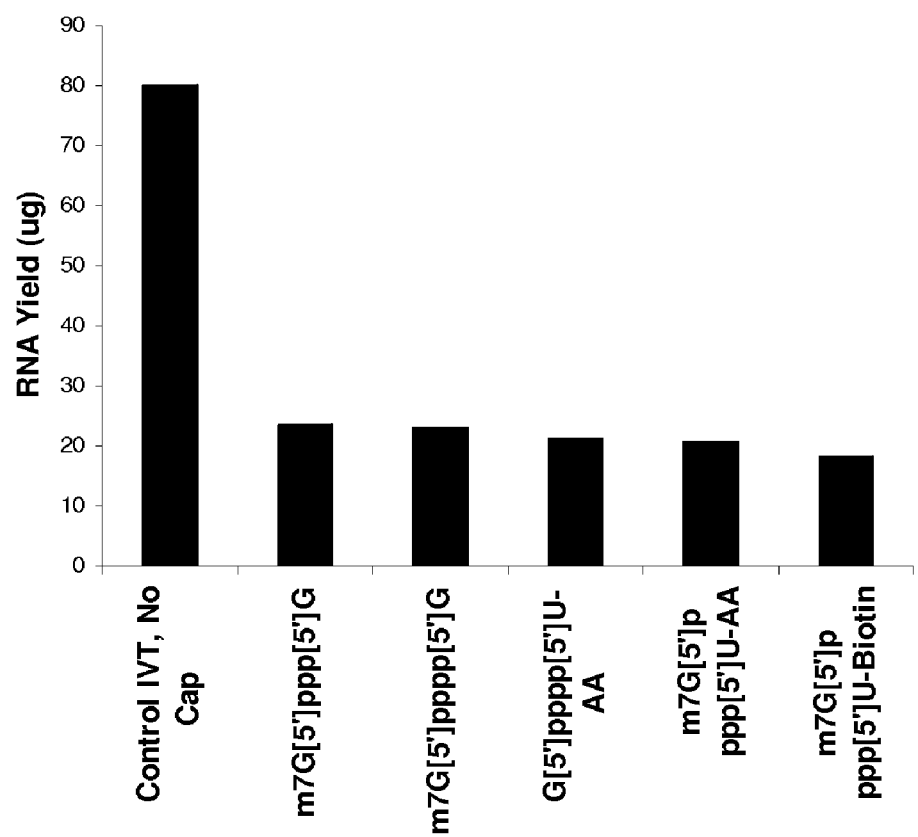
FIG. 10 provides a comparison of transcription yields of RNA cap analogs, analogs with and without linker or linker plus biotin tag.
Figure 11:
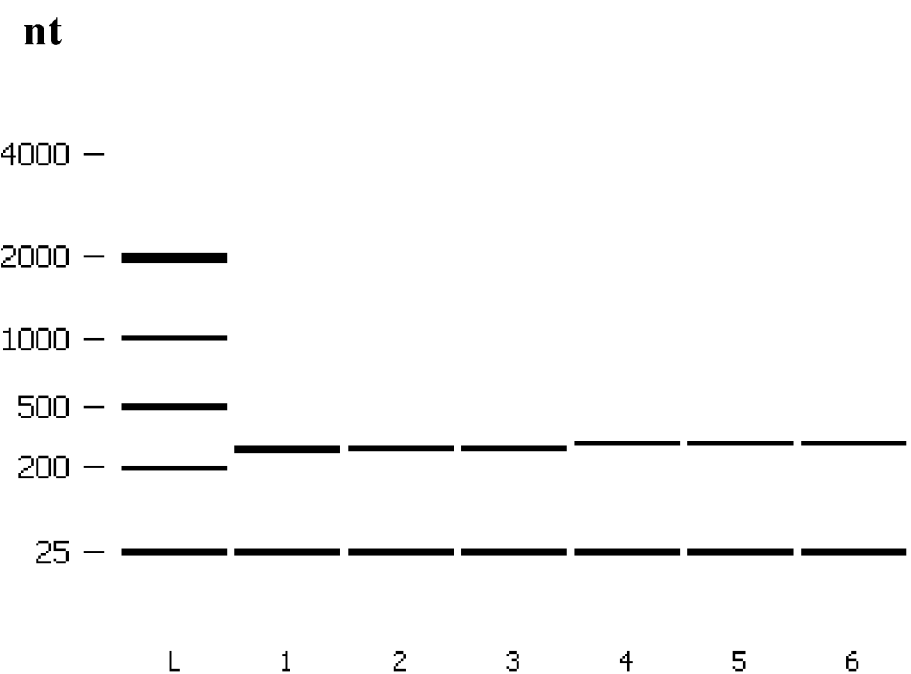
FIG. 11 illustrates the RNA transcript yield obtained from a transcription reaction when using the capped RNA analogs of the present invention.

FIGS. 10 and 11 show the results of selected reporter moiety labeled cap analogs as evaluated in an AmbLuc Poly (A) (Ambion) in vitro transcription assay. The cap analogs transcription yields were comparable for modified and standard cap analogs. As shown in FIG. 11, analysis of each transcribed mRNA indicates that all the mRNAs are not degraded and retain great integrity. Assays were performed on an Agilent 2100 Bioanalyzer.

In some embodiments, the cap analog is used for the synthesis of 5' capped RNA molecules in transcription reactions. Substitution of the cap analog for a portion of the GTP in a transcription reaction results in the incorporation of the cap structure into a corresponding fraction of the transcripts. Capped mRNAs are generally translated more efficiently in reticulocyte lysate and wheat germ in vitro translation systems. It has been found that in vitro transcripts should be capped for microinjection experiments because uncapped mRNAs are rapidly degraded. Cap analogs are also used as a highly specific inhibitor of the initiation step of protein synthesis.

Example 26

Gel Shift Assay

Figure 9:
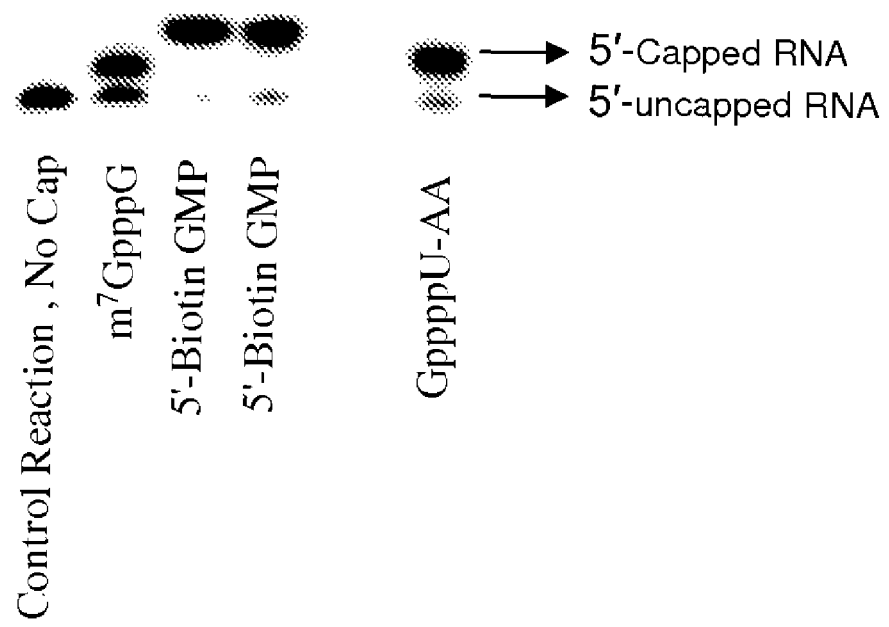
FIG. 9 provides the results of a Gel Shift assay showing greater yields of transcribed RNA and so increased transcription efficiency when RNA is capped vs. uncapped.

A Gel Shift assay was performed by using the MAXIscript™ kit (Ambion, Inc.) following the manufacturer's protocol. The assay determines if the modified cap analogs were substrates for T7 RNA polymerase. Typical 20 μL of T7 RNA polymerase transcriptions contained the following reagents at the final concentrations indicated: linearized pTri β actin vector template, 0.5 μg; ATP, 2 mmol; GTP, 0.4 mmol; 1.6 mmol each CTP and UTP, in a separate reaction; 10× reaction buffer, 4×; T7 RNA polymerase, 50 units/μL; (α-$^{32}$P) ATP, 800 (Ci/mmol); and DEPC water. The control reaction was a normal in vitro transcription reaction, in which no cap analog was added. The transcription reactions were incubated at 37° C. for 2 hr, after which the reaction mixtures were then applied to a 20% dPAGE gel. The assay detects specific structure or size changes described as gel shifts. When structure change or size change occurs it creates complexes that migrate slower during gel electrophoresis than the original complex. As shown in FIG. 9, modified cap compounds were found to be substrates for T7 RNA polymerase, as determined by gel shift assays that clearly revealed that capped RNAs were formed, based on slower migration relative to uncapped RNAs. The new cap G[5']pppp[5']U-AA analogs comprised about 65% of capped RNA.

Although the present disclosure is described with respect to various embodiments and examples, various modifications may be made without departing from the spirit and scope of the invention.

What is claimed:
1. A composition comprising:

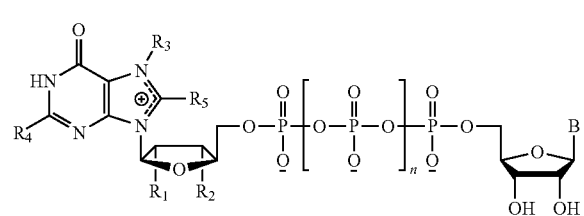

wherein,
B is a nucleobase;
$R_1$ is selected from a halogen, OH, and $OCH_3$;
$R_2$ is selected from H, OH, and $OCH_3$;
$R_3$ is $CH_3$ or void;
$R_4$ is $NH_2$;
$R_5$ is H; and
n is 1, 2 or 3; and
wherein,
a linker is attached to one of $R_1$, $R_2$, $R_4$, $R_5$, or B.
2. The composition as recited in claim 1, wherein said linker is selected from N, S, and O.

3. The composition as recited in claim 2, wherein said linker is selected from an aminoallyl ([—CH$_2$]$_n$CH$_2$NH$_2$) where n=2-18, a secondary amine and an alkyl (C$_3$-C$_{10}$)NH$_2$ chain.

4. The composition as recited in claim 2, further comprising a reporter moiety attached to said linker.

5. The composition as recited in claim 4, wherein said reporter moiety is selected from an affinity tag and an epitope tag.

6. The composition as recited in claim 5, wherein said affinity tag is selected from biotin, iminobiotin, avidin, and streptavidin.

7. The composition as recited in claim 6, wherein said biotin is selected from C$_5$-C$_{20}$-biotin, SS-biotin, XX-biotin, and NHS ester compounds thereof.

8. The composition as recited in claim 1, wherein
R$_3$ is void,
the nucleobase is selected from the group consisting of a pyrimidine, a pyrimidine nucleobase analog, a purine, a purine nucleobase analog, and natural, synthetic and derivative nucleobases thereof,
a) a linker is attached to one of the pyrimidine or purine nucleobases, and
b) a reporter moiety is attached to the linker.

9. The composition as recited in claim 8, wherein said reporter moiety is an affinity tag selected from biotin, iminobiotin, avidin, and streptavidin.

10. The composition as recited in claim 8 attached to the 5' end of an RNA molecule.

11. The composition as recited in claim 1, wherein
R$_3$ is CH$_3$,
the nucleobase is selected from the group consisting of a pyrimidine, a pyrimidine nucleobase analog, a purine, a purine nucleobase analog, and natural, synthetic and derivative nucleobases thereof,
a) a linker is attached to one of the pyrimidine or purine nucleobases, and
b) a reporter moiety is attached to the linker.

12. The composition as recited in claim 11, wherein said reporter moiety is an affinity tag selected from biotin, iminobiotin, avidin, and streptavidin.

13. The composition as recited in claim 11 attached to the 5' end of an RNA molecule.

14. The composition as recited in claim 1, wherein R$_3$ is CH$_3$, the nucleobase is selected from the group consisting of a pyrimidine, a pyrimidine nucleobase analog, a purine, a purine nucleobase analog, and natural, synthetic and derivative nucleobases thereof,
a) a linker is attached to one of R$_1$, R$_2$, R$_4$, or R$_5$, and
b) a reporter moiety is attached to the linker.

15. The composition as recited in claim 14, wherein said reporter moiety is an affinity tag selected from biotin, iminobiotin, avidin, and streptavidin.

16. The composition as recited in claim 14 attached to the 5' end of an RNA molecule.

17. A method of synthesizing a dinucleotide cap analog comprising:
providing a guanosine nucleoside comprising either a 2' substituent or a 3' substituent and optionally comprising a linker;
phosphorylating the nucleoside, forming a nucleotide;
methylating the nucleotide;
adding a phosphorylated second nucleotide optionally comprising a linker;
coupling said first nucleotide with said second nucleotide, forming a dinucleotide cap analog.

18. A method for isolating a dinucleotide capped molecule comprising:
a) providing a nucleic acid mixture containing the composition as recited in claim 10;
b) binding the reporter moiety of step a) to a substrate;
c) extracting the complex of step b) from the nucleic acid mixture;
d) removing the linker from the capped nucleic acid; and
wherein capped nucleic acids are isolated.

19. A composition comprising:
an antigen presenting cell transfected with the composition of claim 1.

20. A kit for capping an RNA transcript comprising a cap analog having the structure:

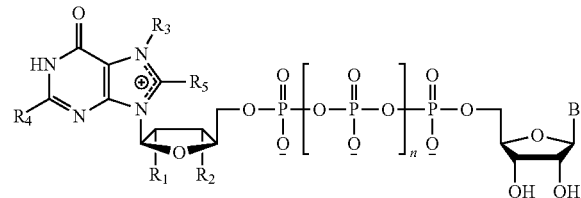

wherein,
B is a nucleobase;
R$_1$ is selected from a halogen, OH, and OCH$_3$;
R$_2$ is selected from OH, OCH$_3$, and H;
R$_3$ is CH$_3$ or void;
R$_4$ is NH$_2$;
R$_5$ is H; and
n is 1, 2 or 3;
and wherein,
a linker is attached to one of R$_1$, R$_2$, R$_4$, R$_5$, or B;
a reporter moiety is attached to the linker;
at least R$_1$, or R$_2$ is OH; and
b) an RNA polymerase.

* * * * *